(12) United States Patent
Kaneko et al.

(10) Patent No.: US 11,442,014 B2
(45) Date of Patent: Sep. 13, 2022

(54) SPECTROSCOPIC ANALYSIS APPARATUS

(71) Applicant: OLYMPUS CORPORATION, Tokyo (JP)

(72) Inventors: Shoichi Kaneko, Tokyo (JP); Akira Sato, Tokyo (JP); Chikashi Ota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/173,332

(22) Filed: Feb. 11, 2021

(65) Prior Publication Data
US 2021/0190686 A1 Jun. 24, 2021

Related U.S. Application Data

(63) Continuation of application No. PCT/JP2018/036233, filed on Sep. 28, 2018.

(51) Int. Cl.
*G01N 21/64* (2006.01)
*G01N 21/65* (2006.01)

(52) U.S. Cl.
CPC .......... *G01N 21/645* (2013.01); *G01N 21/65* (2013.01); *G01N 2021/6484* (2013.01); *G01N 2201/088* (2013.01)

(58) Field of Classification Search
CPC ............................................. G01M 11/31–319
See application file for complete search history.

(56) References Cited

U.S. PATENT DOCUMENTS 6,259,517 B1 * 7/2001 Tedesco ............. G01M 11/3109
356/73.1
2004/0173733 A1 * 9/2004 Korn .................. A61B 1/00057
250/227.11
(Continued)

FOREIGN PATENT DOCUMENTS

EP 2586358 A1 5/2013
JP S57-211034 A 12/1982
(Continued)

OTHER PUBLICATIONS

International Search Report dated Nov. 13, 2018 issued in PCT/JP2018/036233.
(Continued)

*Primary Examiner* — Hina F Ayub
(74) *Attorney, Agent, or Firm* — Scully, Scott, Murphy & Presser, P.C.

(57) ABSTRACT

Provided is a spectroscopic analysis apparatus including: an optical probe; and a spectroscopic analysis portion to which the optical probe is attached. The optical probe includes an optical fiber that guides illumination light coming from a light source and signal light coming from an observation target and an optical member that is disposed at least at a distal end of the optical fiber. The spectroscopic analysis portion includes an information separation portion that generates wavelength dependent characteristics by optically dispersing the signal light and that separates, from information about the signal light, information about first return light returning from the optical member and information about second return light returning from the optical fiber, a problem determining portion that determines a problem occurring at the optical probe based on the separated first return light and second return light, and a notification portion that notifies information about the determined problem.

4 Claims, 37 Drawing Sheets

(56) References Cited

U.S. PATENT DOCUMENTS

| | | | |
|---|---|---|---|
| 2007/0149858 A1 | 6/2007 | Ogawa et al. | |
| 2008/0283770 A1 | 11/2008 | Takahashi | |
| 2010/0252737 A1 | 10/2010 | Fournel et al. | |
| 2012/0190990 A1 | 7/2012 | Ohzawa et al. | |
| 2013/0235369 A1* | 9/2013 | Koifman ................ | G01M 11/31 356/73.1 |
| 2016/0206210 A1 | 7/2016 | Toriyama et al. | |
| 2018/0139370 A1 | 5/2018 | Ichiki et al. | |
| 2018/0228353 A1 | 8/2018 | Ohara | |
| 2018/0353061 A1 | 12/2018 | Tanaka et al. | |

FOREIGN PATENT DOCUMENTS

| | | |
|---|---|---|
| JP | 2007-175429 A | 7/2007 |
| JP | 2008-284030 A | 11/2008 |
| JP | 2012-147860 A | 8/2012 |
| JP | 2014-232120 A | 12/2014 |
| JP | 2016-028780 A | 3/2016 |
| JP | 2016-071040 A | 5/2016 |
| WO | WO 2015/163100 A1 | 10/2015 |
| WO | WO 2016/052270 A1 | 4/2016 |
| WO | WO 2016/185763 A1 | 11/2016 |
| WO | WO 2017/060992 A1 | 4/2017 |
| WO | 2017/145336 A1 | 8/2017 |

OTHER PUBLICATIONS

Japanese Office action dated Apr. 5, 2022 received in 2020-547790.

* cited by examiner

SPECTROSCOPIC ANALYSIS APPARATUS

CROSS-REFERENCE TO RELATED APPLICATIONS

This is a continuation of International Application PCT/JP2018/036233, with an international filing date of Sep. 28, 2018, which is hereby incorporated by reference herein in its entirety.

TECHNICAL FIELD

The present invention relates to a spectroscopic analysis apparatus.

BACKGROUND ART

As a spectroscopic analysis apparatus utilizing Raman spectroscopy, there is a known spectroscopic analysis apparatus including: an optical probe that is inserted into a body of a patient; and a spectroscopic analysis portion that analyzes signal light acquired by the optical probe (for example, see Japanese Unexamined Patent Application, Publication No. 2016-028780).

SUMMARY OF INVENTION

An aspect of the present invention is a spectroscopic analysis apparatus including: an optical probe; and a spectroscopic analysis portion to which the optical probe is attached in an attachable/detachable manner by means of a connector, wherein the optical probe includes an optical fiber that guides illumination light coming from a light source and signal light coming from an observation target and an optical member that is disposed at least at a distal end of the optical fiber, and the spectroscopic analysis portion includes an information separation portion that generates wavelength dependent characteristics by optically dispersing the signal light and that separates, from information about the signal light, information about first return light returning from the optical member and second return light returning from the optical fiber, a problem determining portion that determines a problem occurring at the optical probe on the basis of the first return light and the second return light separated by the information separation portion, and a notification portion that notifies information about the determined problem.

DESCRIPTION OF EMBODIMENTS

A spectroscopic analysis apparatus 1 according to a first embodiment of the present invention will be described below with reference to the drawings.

Figure 1:
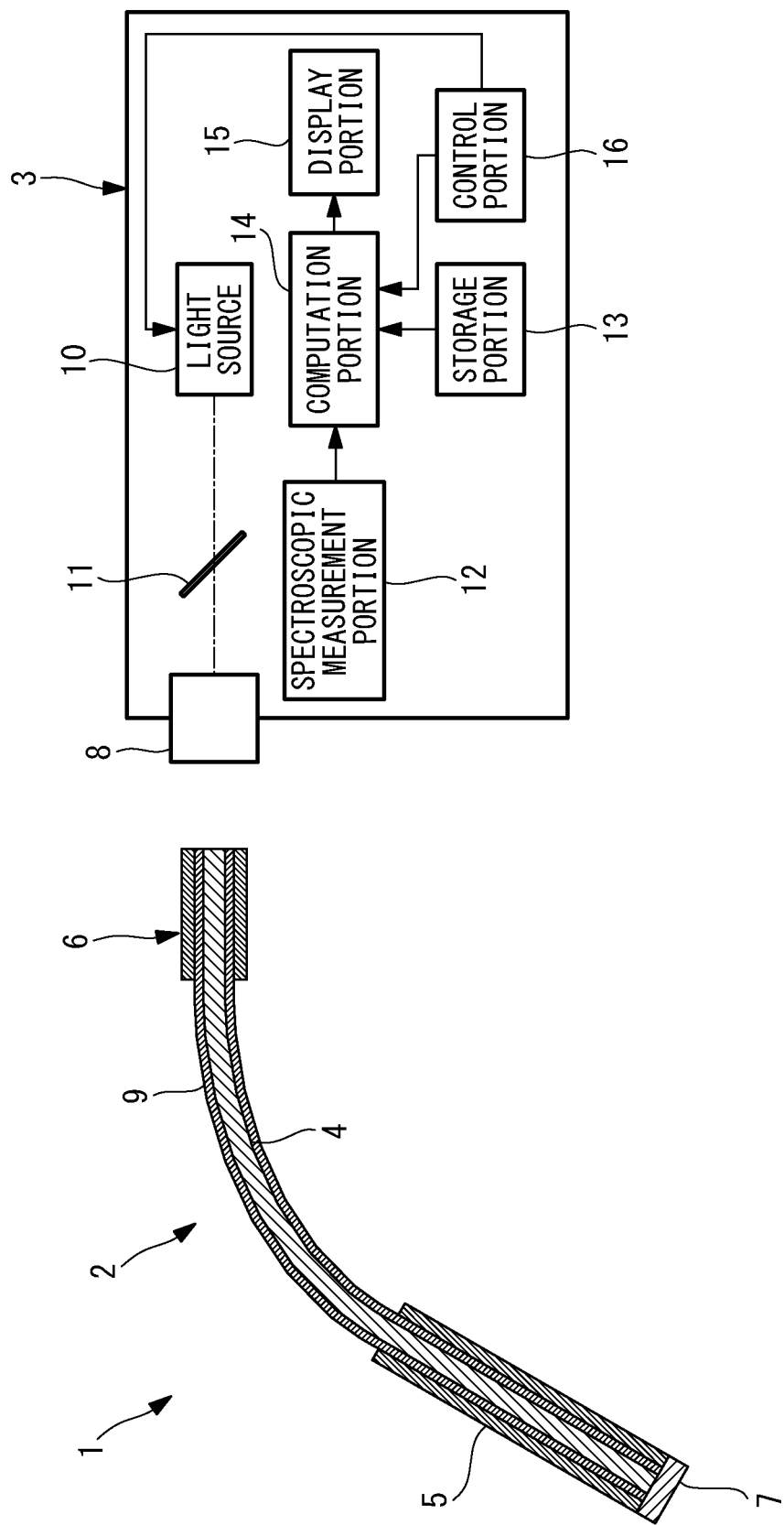
FIG. 1 is a schematic diagram showing a spectroscopic analysis apparatus according to a first embodiment of the present invention.

As shown in FIG. 1, the spectroscopic analysis apparatus 1 according to this embodiment includes an optical probe 2 and a spectroscopic analysis portion 3 that is attached to the optical probe 2 in an attachable/detachable manner.

As shown in FIG. 1, the optical probe 2 includes: an optical fiber 4; a probe head 5 that is disposed at a distal end of the optical fiber 4; and a connector 6 that is disposed at a proximal end of the optical fiber 4. The probe head 5 is cylindrically formed, the optical fiber 4 is disposed in the interior thereof, and a first optical member (optical member) 7 is disposed at a position facing the distal end of the optical fiber 4. The optical fiber 4 is formed of, for example, fused silica, and the first optical member 7 is formed of, for example, sapphire.

The connector 6 is cylindrically formed to be connected to a receiving-side connector 8 included in the spectroscopic analysis portion 3. The optical probe 2 and the connector 6 are connected by means of the optical fiber 4 and a sheath 9 that covers the optical fiber 4.

The spectroscopic analysis portion 3 includes: the receiving-side connector 8 that is connected to the connector 6 of the optical probe 2; a light source 10 that generates illumination light and that makes the generated illumination light enter the optical probe 2 connected to the receiving-side connector 8; a dichroic mirror 11 that is disposed between the receiving-side connector 8 and the light source 10, that allows the illumination light to pass therethrough, and that reflects, of return light coming from an optical probe 2 side, light having a longer wavelength than the illumination light; a spectroscopic measurement portion 12 that generates wavelength dependent characteristics by spectrally dispersing the reflected return light; a storage portion 13; a computation portion (information separation portion, problem determining portion) 14; a display portion (notification portion) 15; and a control portion 16.

The spectroscopic measurement portion 12 consists of a spectrometer (not shown) that spatially separates light according to the wavelength thereof, a photodetector (not shown) such as a CCD camera; and a light-guide optical system (not shown) for guiding, to the spectrometer, the light transmitted to the spectroscopic analysis portion 3 by the optical probe 2.

The computation portion 14 consists of a processor, the storage portion 13 consists of a memory, and the display portion 15 is a monitor. The control portion 16 consists of a processor, an input apparatus, and a signal output apparatus.

The storage portion 13 stores information about a wavelength range that contains Raman scattered light of an observation target X and baselines in accordance with a Raman spectrum of the optical fiber 4 and the specifications of the spectroscopic measurement portion 12.

The spectroscopic analysis portion 3 has functions for executing: a diagnosis mode in which the Raman spectrum of the observation target X is measured after connecting the optical probe 2 to the spectroscopic analysis portion 3 and analysis of the observation target X is performed on the basis of said Raman spectrum; and an examination mode in which a problem in the optical probe 2 itself, such as optical power loss due to damage to the optical fiber 4, and a problem such as optical power loss due to a connection failure that occurs when connecting the optical probe 2 to the spectroscopic analysis portion 3 are examined. An operator can set, via the input apparatus included in the control portion 16, the diagnosis mode and the examination mode to be executed by the spectroscopic analysis portion 3. The control portion 16 has functions for changing the setting of the various types of optical apparatuses built into the spectroscopic analysis portion 3 and for controlling changing of computing functions in the computation portion 14 in accordance with the respective modes set by the operator.

The examination mode is normally performed before the diagnosis mode in which the Raman spectrum of the observation target X is measured. The examination mode is performed without disposing the observation target X at the distal end of the optical probe 2 after connecting the optical probe 2 to the spectroscopic analysis portion 3. After confirming that there is no problem regarding optical power loss at the optical probe 2 itself or optical power loss that occurs due to the connection of the optical probe 2 to the spectroscopic analysis portion 3 as a result of performing the examination mode, the operator can execute the diagnosis mode.

Figure 2:
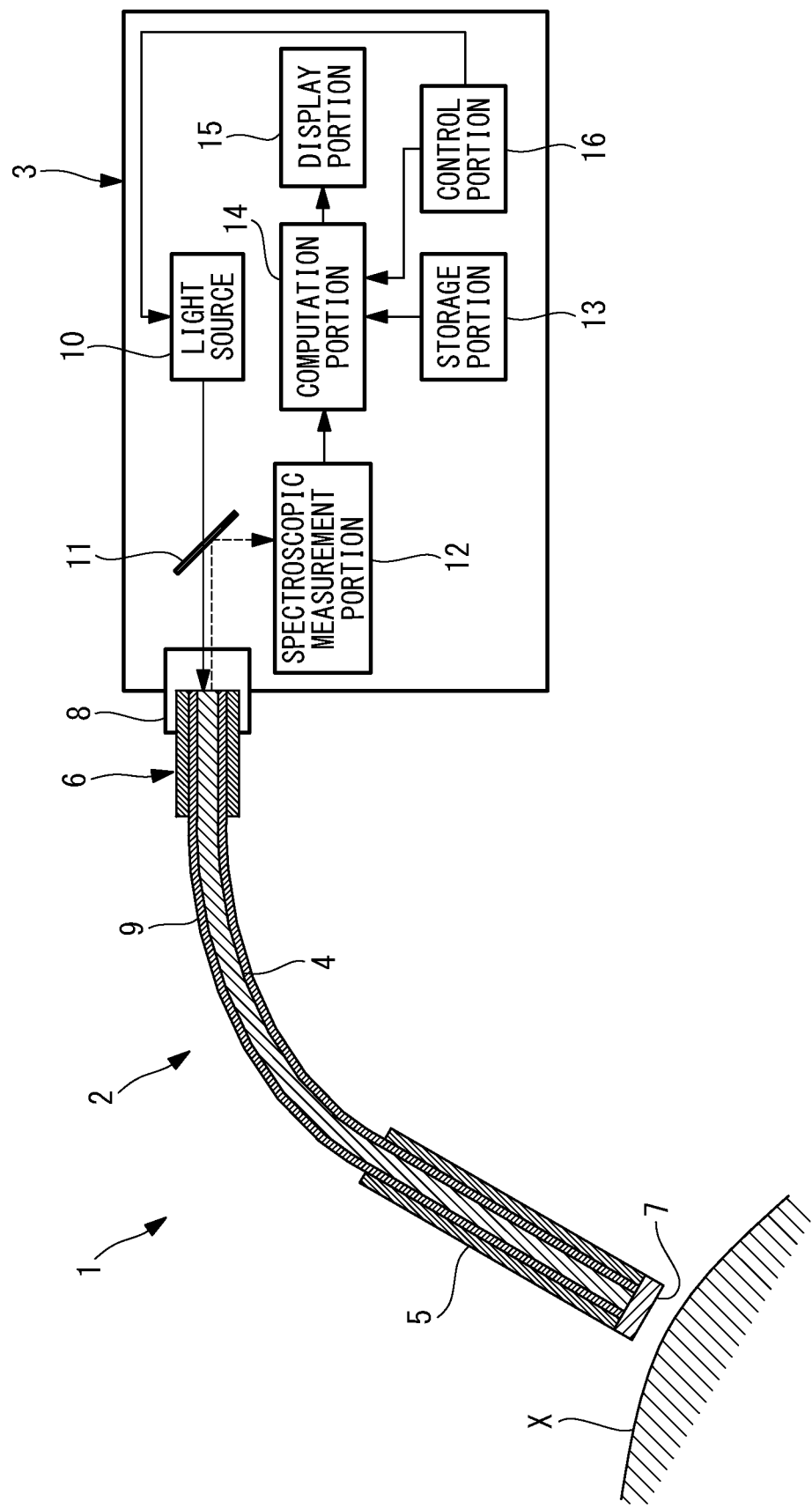
FIG. 2 is a schematic diagram for explaining a diagnosis mode of an observation target, the diagnosis mode being performed by employing the spectroscopic analysis apparatus in FIG. 1.
Figure 3:
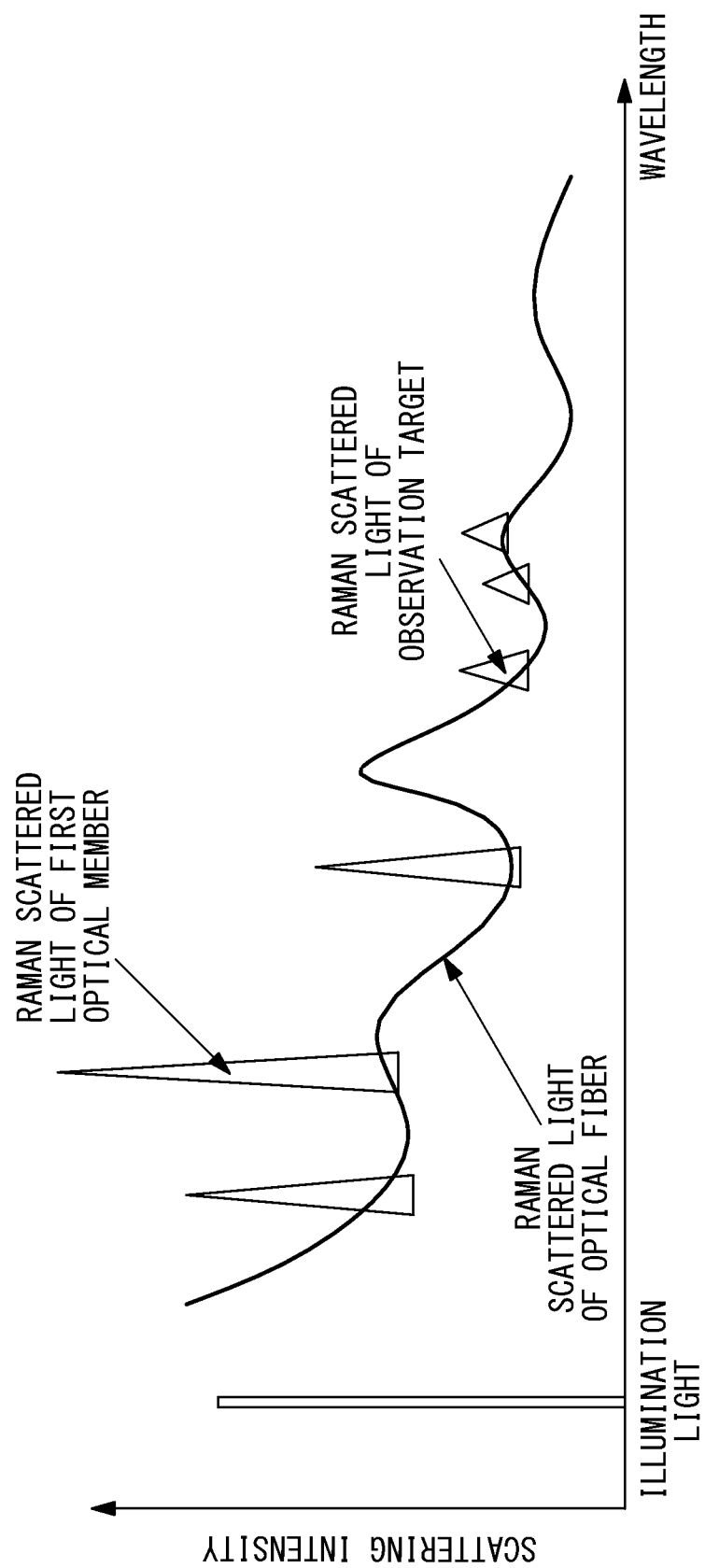
FIG. 3 is a diagram showing illumination light radiated by the spectroscopic analysis apparatus in FIG. 1 and a spectrum of acquired Raman scattered light.

Because the optical probe 2 includes the optical fiber 4 and the first optical member 7, as shown in FIG. 2, when the illumination light coming from the light source 10 enters the optical probe 2, Raman scattered light beams having different spectral shapes are radiated from the optical fiber 4 and the first optical member 7. In other words, when the illumination light is emitted from the light source 10 after connecting the connector 6 of the optical probe 2 to the receiving-side connector 8 of the spectroscopic analysis portion 3 and disposing the observation target X at the distal end of the optical probe 2, the illumination light is radiated onto the observation target X via the optical probe 2, and a Raman scattered light beam that is generated while the illumination light is being guided through the optical fiber 4 of the optical probe 2, a Raman scattered light beam that is generated when the illumination light passes through the first optical member 7, a Raman scattered light beam (signal light) that is generated at the observation target X, and a portion of the illumination light return toward the spectroscopic analysis portion 3 from the optical probe 2 side as return light, as shown in FIG. 3.

The constituent material of the optical fiber 4 is silica or a plastic, and an inorganic crystal, such as optically transparent sapphire or fused silica, a plastic, and so forth can be employed as the material for the first optical member 7. In the case in which the observation target X is biological tissue, it is desirable that the plastic be a fluoroplastic. So long as the constituent material of the optical fiber 4 and the constituent material of the first optical member 7 are different, Raman scattered light beams having different spectrum shapes would be radiated.

Figure 7:
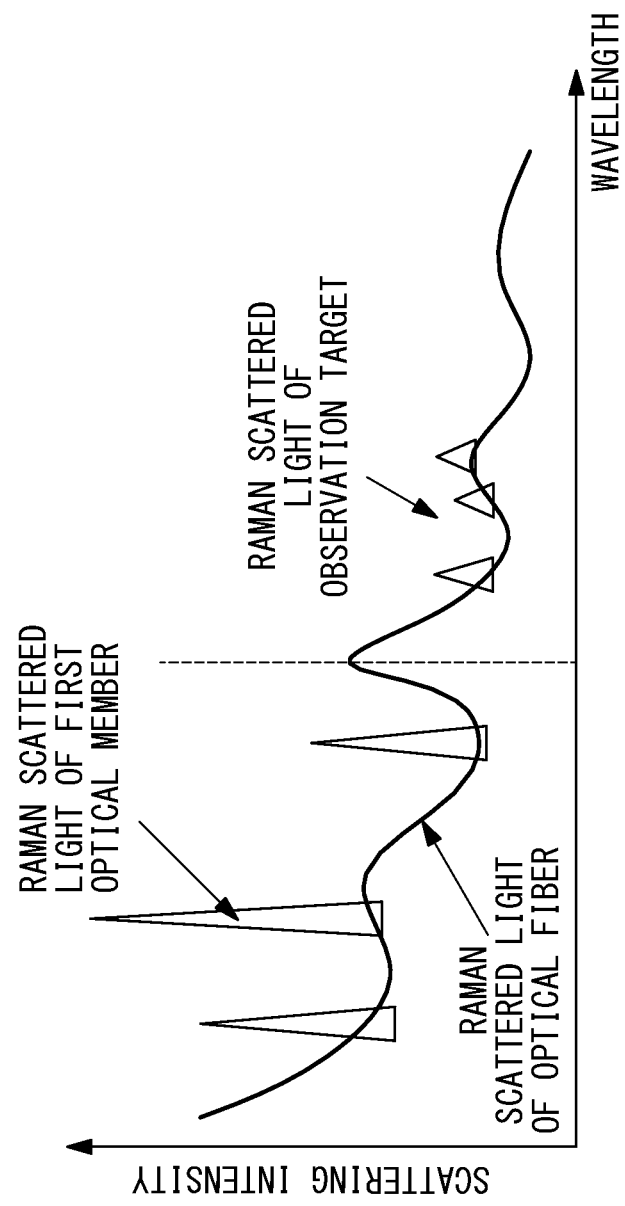
FIG. 7 is a diagram showing a spectrum of the Raman scattered light in which a spectrum of the illumination light is excluded from the spectrum in FIG. 3.

Because the dichroic mirror 11 allows the illumination light to pass therethrough, as shown in FIG. 7, the illumination light beam among the return light is removed by passing through the dichroic mirror 11, the examination light consisting of the Raman scattered light beams of the observation target X, the first optical member 7, and the optical fiber 4 is reflected and enters the spectroscopic measurement portion 12.

In the diagnosis mode, a Raman spectrum of the return light coming from the optical probe 2 side, which is measured by the spectroscopic measurement portion 12, is as shown in FIG. 7. The spectrum shown in FIG. 7 has a waveform that schematically represents the Raman spectrum of the return light in the case in which the constituent material of the optical fiber is silica, the first optical member is an optically transparent inorganic crystal (sapphire), and the observation target is biological tissue; and said spectrum has a waveform in which a Raman spectrum of the optical fiber having a broad peak linewidth at a relatively low frequency, a Raman spectrum of the first optical member having a narrow peak linewidth at a higher frequency, and a Raman spectrum of the observation target are superimposed on each other.

The Raman spectrum of the measured return light is input to the computation portion 14.

The computation portion 14 has computing functions corresponding to the diagnosis mode and the examination mode, which are two modes having different operations.

In the diagnosis mode, the computation portion 14 subtracts the contributions of the Raman scattered light beams generated at the first optical member 7 and the optical fiber 4 from the input Raman spectrum of the return light.

Figure 8:
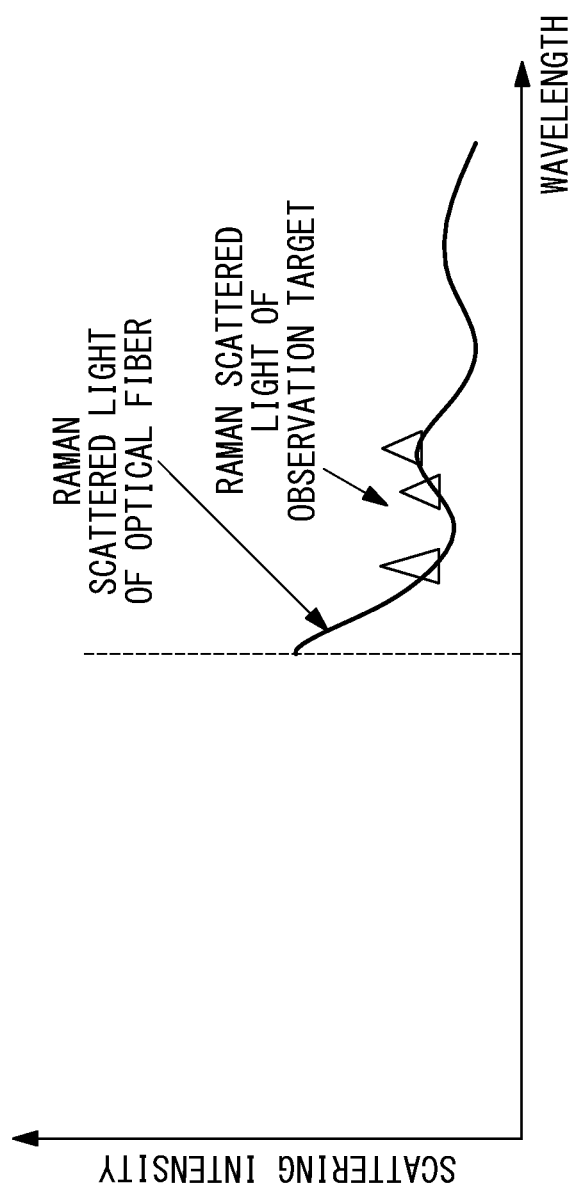
FIG. 8 is a diagram showing a spectrum in which a spectrum in a wavelength range containing Raman scattered light of the first optical member is excluded from the spectrum in FIG. 7.
Figure 9:
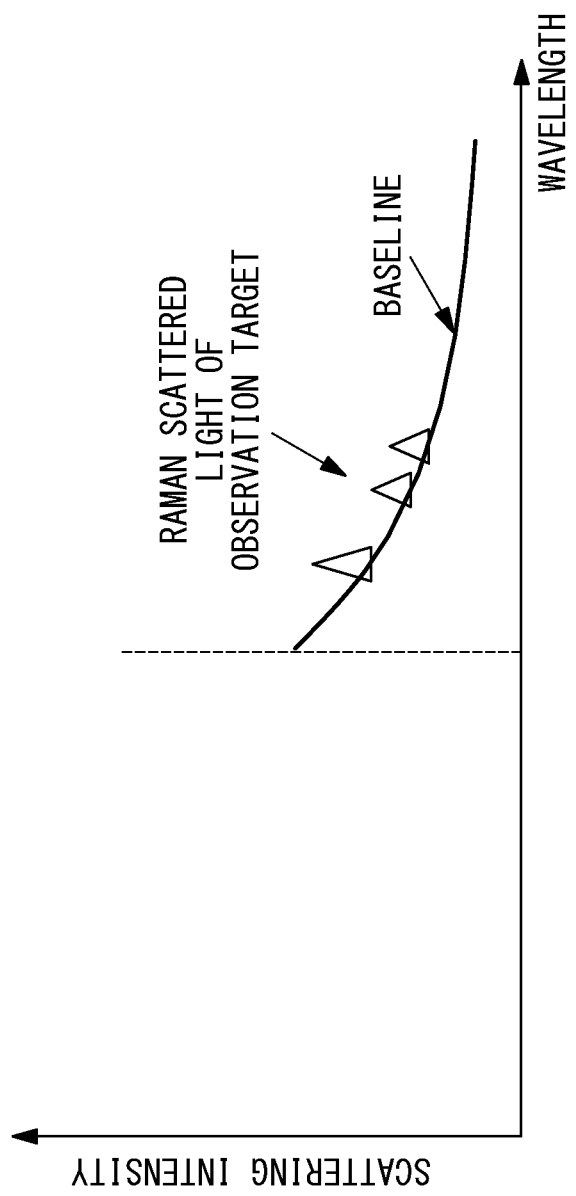
FIG. 9 is a diagram showing a spectrum in which a spectrum of Raman scattered light of the optical fiber is excluded from the spectrum in FIG. 8.
Figure 10:
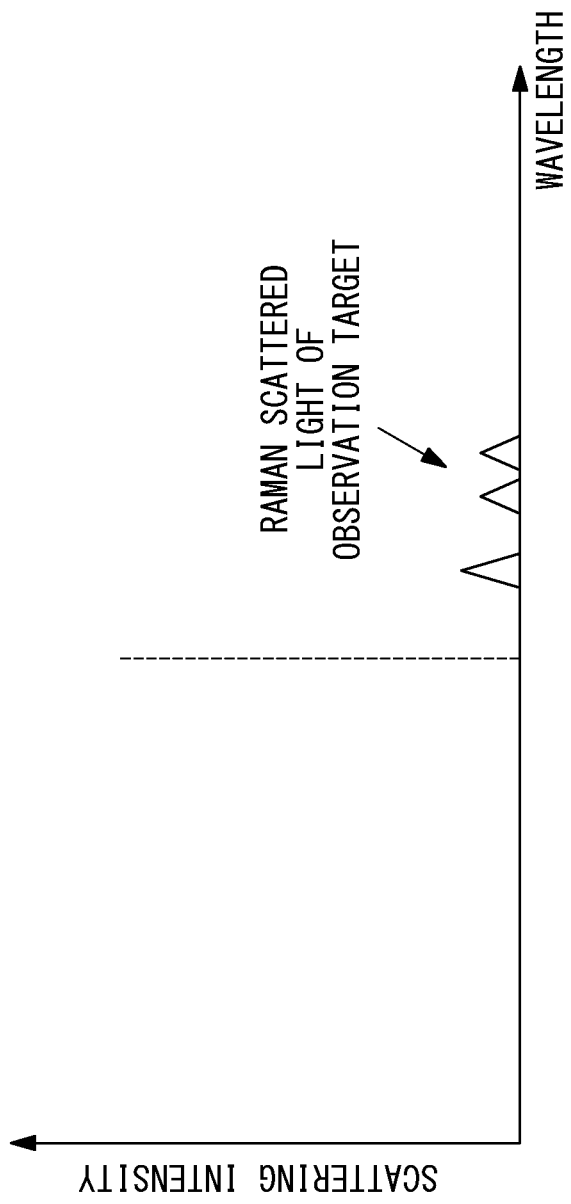
FIG. 10 is a diagram showing a spectrum of Raman scattered light of the observation target in which a baseline is excluded from the spectrum in FIG. 9.

Specifically, the computation portion 14 removes, on the basis of the information about the wavelength range contained in the Raman scattered light beam of the observation target X, which is stored in the storage portion 13 in advance, the Raman spectrum of the wavelength range that contains the Raman scattered light of the first optical member 7 from the input Raman spectrum of the return light, as shown in FIG. 8. Next, as shown in FIG. 9, the computation portion 14 removes the Raman spectrum of the optical fiber 4 stored in the storage portion 13. Then, as shown in FIG. 10, the computation portion 14 subtracts the baseline stored in the storage portion 13 from the resultant Raman spectrum.

Accordingly, it is possible to obtain the Raman spectrum of the observation target X. It is possible to calculate a component ratio of the observation target X from the obtained Raman spectrum of the observation target X. Alternatively, it is possible to calculate, for example, an analysis result such as a score that represents a quantified severity of a lesion in the observation target X on the basis of said component ratio.

The display portion 15 displays the Raman spectrum of the observation target X itself, which has been calculated by the computation portion 14, the component ratio of the observation target X calculated from the Raman spectrum, or the score calculated on the basis of the component ratio of the observation target X.

Figure 4:
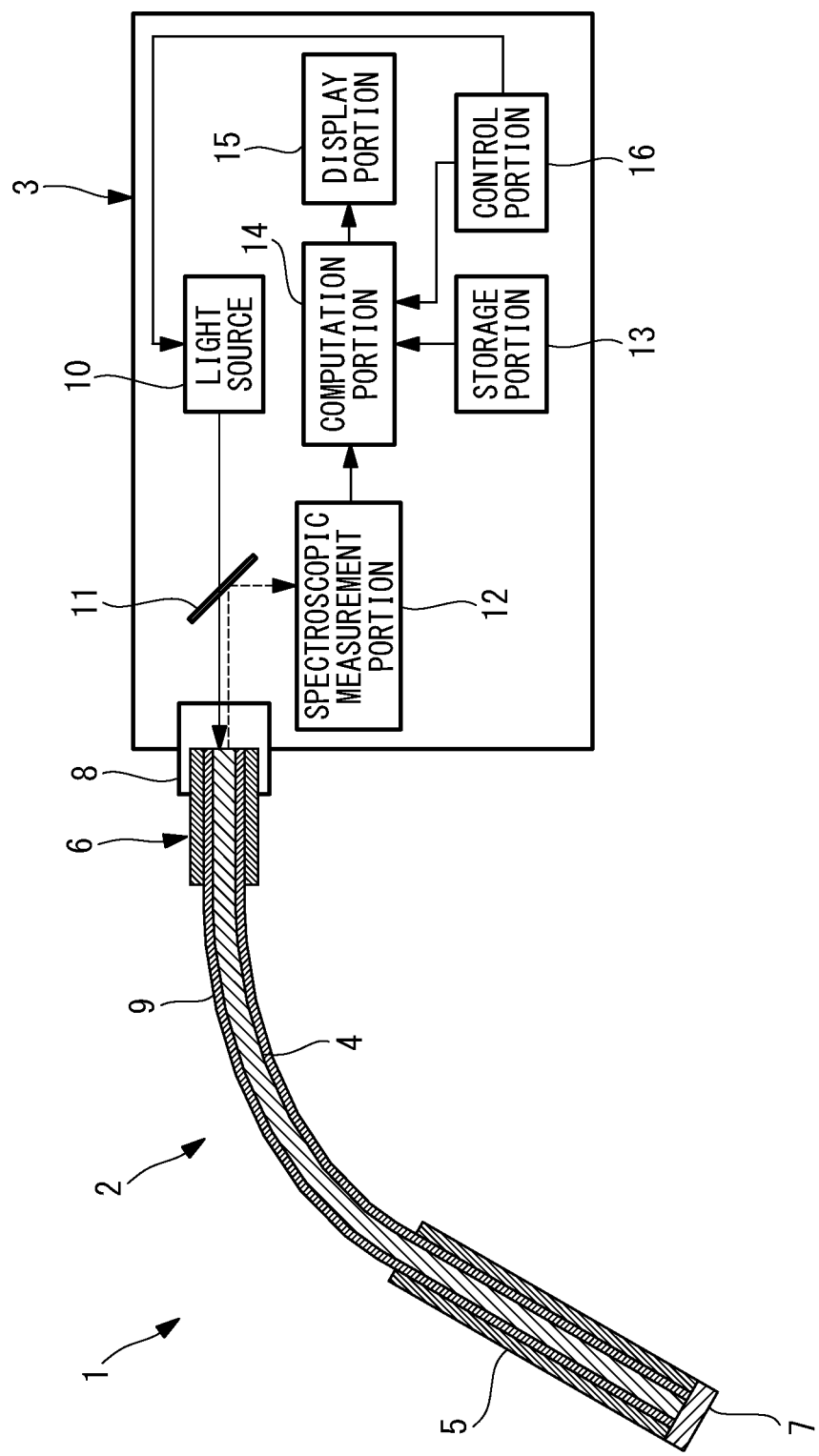
FIG. 4 is a schematic diagram for explaining an examination mode employing the spectroscopic analysis apparatus in FIG. 1.

In the examination mode, the illumination light is emitted from the light source 10 without disposing the observation target X at the distal end of the optical probe 2. Accordingly, the Raman scattered light beam generated while the illumination light is being guided through the optical probe 2, the Raman scattered light beam generated when the illumination light passes through the first optical member 7, and a portion of the illumination light return toward the spectroscopic analysis portion 3 from the optical probe 2 side as the return light, as shown in FIG. 4.

Also, because the dichroic mirror 11 allows the illumination light to pass therethrough, the illumination light in the return light is removed as a result of passing therethrough, the examination light consisting of the Raman scattered light beams of the first optical member 7 and the optical fiber 4 is reflected and is made to enter to the spectroscopic measurement portion 12.

The spectroscopic measurement portion 12 detects a Raman spectrum of the incident examination light.

The detected Raman spectrum is input to the computation portion 14.

Figure 11:
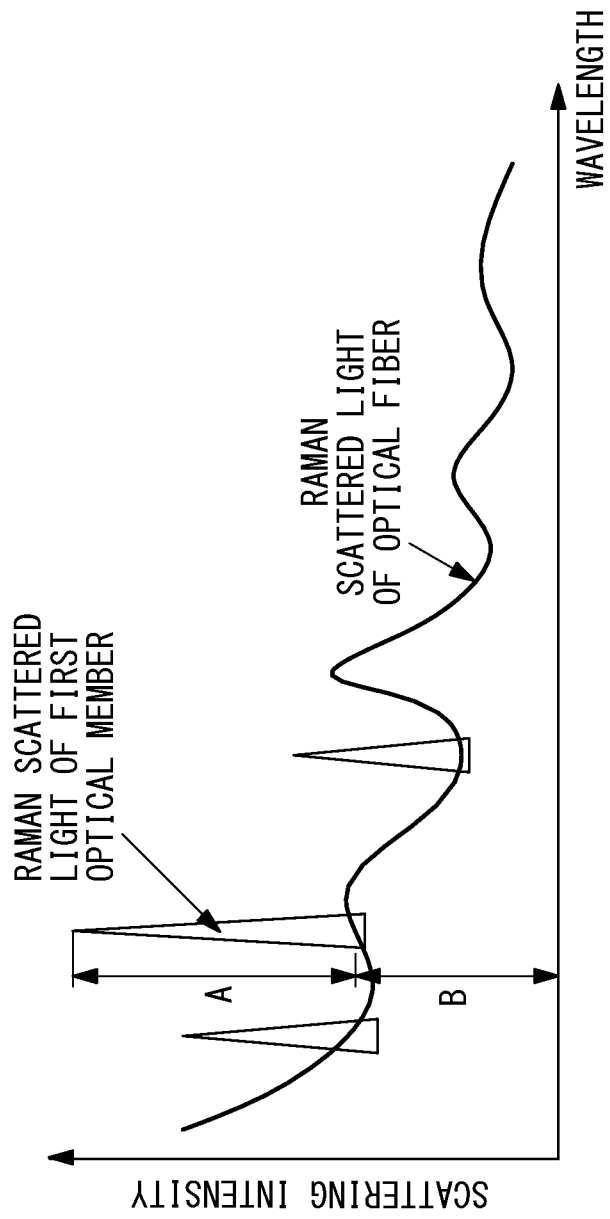
FIG. 11 is a diagram showing the intensity of the Raman scattered light of the first optical member and that of the optical fiber that are used in the problem determination in this embodiment.

In the examination mode, as shown in FIG. 11, the computation portion 14: determines, from the input Raman spectrum of the examination light, the examination-light intensity of the Raman scattered light of the first optical member 7 at an arbitrary peak wavelength, in other words, Sab (=A+B), which is the sum of a Raman scattering intensity A of the first optical member 7 and a Raman scattering intensity B of the optical fiber 4 at the arbitrary peak wavelength; identifies the intensity B of the Raman scattered light of the optical fiber 4 at the above-described wavelength from the spectrum of Raman scattered light of the optical fiber 4 stored in the storage portion 13; and calculates the ratio Rab (=A/B) of the intensity A of the Raman scattered light of the first optical member 7 and the intensity B of the Raman scattered light of the optical fiber 4. Alternatively, in the case in which there is a considerable difference between the peak frequency of the Raman spectrum of the first optical member 7 and the peak frequency of the Raman spectrum of the optical fiber 4, the Raman spectrum of the first optical member 7 and the Raman spectrum of the optical fiber 4 may be separated from the Raman spectrum of the examination light by means of a frequency filter.

Also, the computation portion 14 compares the intensity Sab with a threshold TS1 and a threshold TS2 stored in the storage portion 13, compares the ratio Rab with a threshold TR1 and a threshold TR2 stored in the storage portion 13, and thus, the computation portion 14 determines the presence/absence of a problem in accordance with the comparison results as described below. The display portion 15 displays the determination results of the computation portion 14.

Here, the Raman scattering intensities of the examination light detected by the spectroscopic measurement portion 12 will be described.

Figure 5:
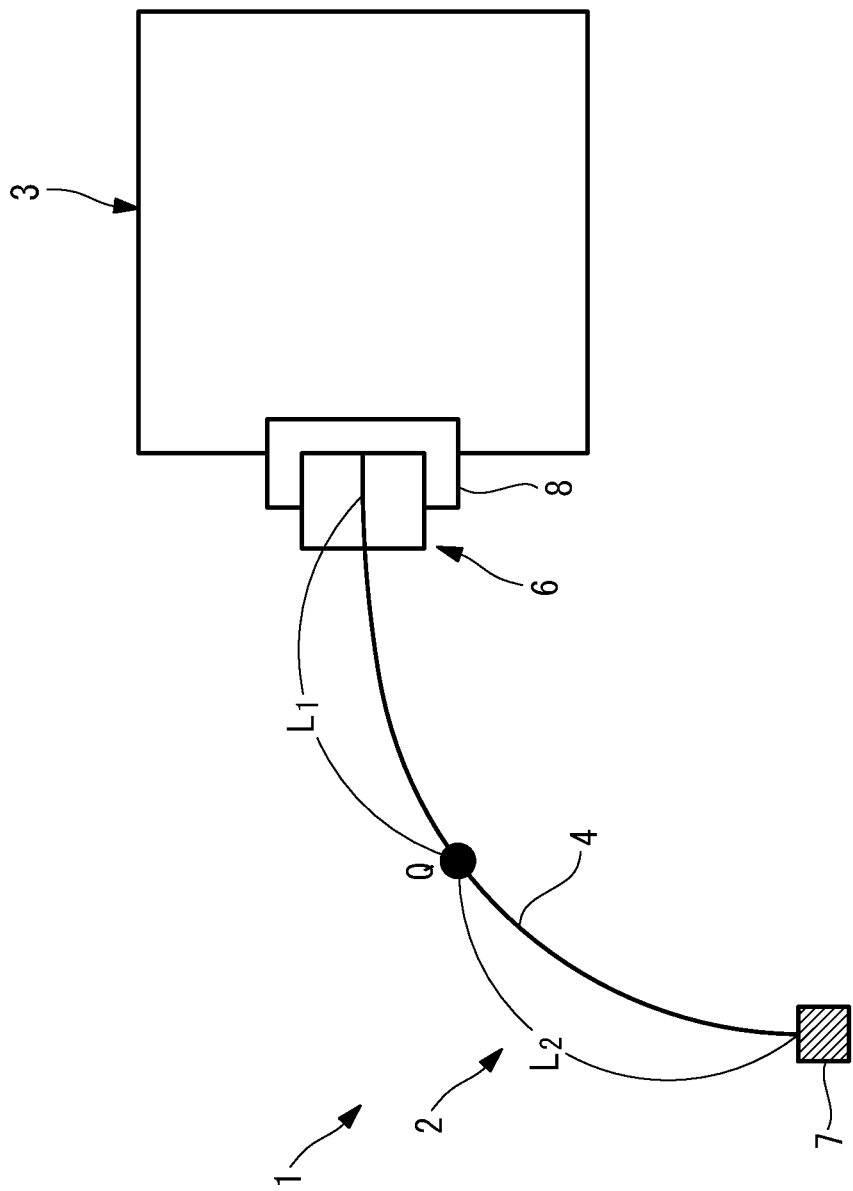
FIG. 5 is a schematic diagram showing the relationship between the arrangement of a first optical member, an optical fiber, a connector, and a receiving-side connector and the position of a point Q at which the optical transmission efficiency changes in the optical fiber in the examination mode of the observation target, the examination mode being performed by employing the spectroscopic analysis apparatus in FIG. 1.

FIG. 5 schematically shows the arrangement of the spectroscopic analysis portion 3, the connector 6 of the optical probe 2, the receiving-side connector 8 of the spectroscopic analysis portion 3, the optical probe 2, and the first optical member 7 in the spectroscopic analysis apparatus according to this embodiment. Optical power loss occurs in the optical connection between the connector 6 of the optical probe 2 and the receiving-side connector 8 of the spectroscopic analysis portion 3. Optical power loss is assumed to be occurring, due to damage to the optical fiber 4, at the position of a point Q on the optical probe 2.

In FIG. 5, the length of the optical fiber 4 from the connecting position of the optical probe 2 and the spectroscopic analysis portion 3 to the position of the point Q is assumed to be $L_1$, and the length of the optical fiber 4 from the position of the point Q to the first optical member 7 disposed at the distal end of the optical probe 2 is assumed to be $L_2$. The total length of the optical fiber 4 is assumed to be L ($L=L_1+L_2$).

Here, the optical transmission efficiency of the optical connection of the spectroscopic analysis portion 3 and the optical probe 2 is assumed to be $\eta (0<\eta<1)$, the optical transmission efficiency at the position of the point Q is assumed to be $\alpha (0<\alpha<1)$, and the light reflection efficiency at a distal-end surface of the optical probe 2 is assumed to be $\gamma (0<\gamma<1)$.

The Raman-scattered-light generation efficiency in the first optical member 7 is assumed to be $\sigma_1$ and the Raman-scattered-light generation efficiency in the optical fiber 4 of the optical probe 2 is assumed to be $\sigma_g$. The optical input power to the optical probe 2 from the spectroscopic analysis portion 3 is assumed to be P.

When the various parameters are determined as described above, of the examination light detected by the spectroscopic measurement portion 12, the light intensity due to the Raman scattering of various members is approximated by a sum of intensities of light components of Expression (1) to Expression (3) below.

Of the Raman scattered light generated by the illumination light guided to the distal end of the optical probe 2 from the proximal end thereof, a light component $L_{P1}$ that returns to the spectroscopic analysis portion 3 without passing through the distal end of the optical probe 2 is expressed by Expression (1) below.

$$L_{P1}=L_1\sigma_g\eta^2 P+L_2\sigma_g\alpha^2\eta^2 P+\sigma_1\alpha^2\eta^2 P \tag{1}$$

Of the Raman scattered light generated by the illumination light guided to the distal end of the optical probe 2 from the proximal end thereof, a light component $L_{P2}$ that returns to the spectroscopic analysis portion 3 by being reflected at the distal end of the optical probe 2 is expressed by Expression (2) below.

$$L_{P2}=\gamma\alpha^2\eta^2 P(\sigma_1+\sigma_g L) \tag{2}$$

Of the Raman scattered light generated by the illumination light guided to the proximal end of the optical probe 2 from the distal end thereof, a light component $L_{P3}$ that returns to the spectroscopic analysis portion 3 without passing through the distal end of the optical probe 2 is expressed by Expression (3) below.

$$L_{P3}=\gamma\alpha^2\eta^2 P(\sigma_1+\sigma_g L) \tag{3}$$

Therefore, a Raman scattering intensity Pobs of the examination light detected by the spectroscopic measurement portion 12 is approximated by Expression (4) below.

$$Pobs=L_1\sigma_g\eta^2 P+L_2\sigma_g\alpha^2\eta^2 P+\sigma_1\alpha^2\eta^2 P+2\gamma\alpha^2\eta^2 P(\sigma_1+\sigma_g L)=(1+2\gamma)\alpha^2\eta^2 P\sigma_1+(L_1\eta^2+L_2\alpha^2\eta^2+2\gamma\alpha^2\eta^2 L)P\sigma_g \tag{4}$$

Here, regarding Expression (4) that represents the Raman scattering intensity Pobs of the examination light, described above, Pobs of the Raman scattered light of the first optical member 7 at the arbitrary peak wavelength is Sab(A+B). The ratio of the Raman scattering intensity due to the first optical member 7, in other words, the term including $\sigma_1$ in Expression (4) representing Pobs, and the Raman scattering intensity due to the optical fiber 4, in other words, the term including $\sigma_g 2$ in Expression (4) representing Pobs, is Rab (A/B).

Here, because Sab or Rab at the Raman scattering intensity detected by the spectroscopic measurement portion 12 varies depending on the optical connection realized between the receiving-side connector 8 of the spectroscopic analysis portion 3 and the connector 6 of the optical probe 2 or the optical power loss in the optical fiber of the optical probe 2, it is possible to identify a specific site at which a optical power loss problem is occurring on the basis of the Raman spectrum of the examination light. This fact will be explained below, in detail, by way of cases 1 to 4 with different conditions.

Case 1

The case in which optical power losses in the spectroscopic analysis portion 3 and the connector 6 of the optical probe 2 are negligible and an power loss at optical fiber in the optical probe 2 is also negligible, in other words, the case in which $\eta \approx 1$ and $\alpha \approx 1$, will be described.

In this case, a Raman scattering intensity ST1 of the examination light detected by the spectroscopic measurement portion 12 is expressed by Expression (5) below.

$$ST1 = (1+2\gamma)P\sigma_1 + (L_1+L_2+2\gamma L)P\sigma_g \quad (5)$$

R11F, which is the ratio of the Raman scattering intensity of the first optical member 7 and the Raman scattering intensity of a member of the optical fiber 4, is expressed by Expression (6) below.

$$R11F = (1+2\gamma)\sigma_1/(L_1+L_2+2\gamma L)\sigma_g \quad (6)$$

Here, although $\sigma_1$ and $\sigma_g$ are functions of wavelength, focusing on an arbitrary peak wavelength $\lambda$ of the Raman scattered light of the first optical member 7, ST1($\lambda$) at that wavelength is Sab and R11F($\lambda$) at that wavelength is Rab. Regarding STi (i=1, 2, 3, and 4), described later, values at a peak wavelength $\lambda$ are Sab, and, similarly, regarding R11F, R21F, R31F, and R41F, described later, values at the peak wavelength $\lambda$ are Rab.

Case 2

The case in which optical power losses in the spectroscopic analysis portion 3 and the connector 6 of the optical probe 2 are present and the power loss at optical fiber in the optical probe 2 is negligible, in other words, the case in which 0<η<1 and α≈1, will be described.

In this case, a total Raman scattering intensity ST2 detected by the spectroscopic measurement portion 12 is expressed by Expression (7) below. Sab is the value of ST2 at the peak wavelength $\lambda$.

$$Sab = ST2(\lambda) = (1+2\gamma)\eta^2 P\sigma_1 + (L_1+L_2+2\gamma L)\eta^2 P\sigma_g = \eta^2 ST1(\lambda) \quad (7)$$

R21F, which is the ratio of the Raman scattering intensity of the first optical member 7 and the Raman scattering intensity of the member of the optical fiber 4, is expressed by Expression (8) below.

$$Rab = R21F(\lambda) = (1+2\gamma)\sigma_1/(L_1+L_2+2\gamma L)\sigma_g \quad (8)$$

Case 3

The case in which optical power losses in the spectroscopic analysis portion 3 and the connector 6 of the optical probe 2 are negligible and an power loss at optical fiber in the optical probe 2 is present, in other words, the case in which η≈1 and 0<α<1, will be described.

In this case, a total Raman scattering intensity ST3 detected by the spectroscopic measurement portion 12 is expressed by Expression (9) below. Sab is the value of ST3 at the peak wavelength $\lambda$.

$$Sab = ST3(\lambda) = (1+2\gamma)\alpha^2 P\sigma_1 + (L_1+L_2\alpha^2+2\gamma\alpha^2 L)P\sigma_g \quad (9)$$

R31F, which is the ratio of the Raman scattering intensity of the first optical member 7 and the Raman scattering intensity of the optical fiber 4, is expressed by Expression (10) below.

$$Rab = R31F(\lambda) = (1+2\gamma)\alpha^2\sigma_1/(L_1+L_2\alpha^2+2\gamma\alpha^2 L)\sigma_g \quad (10)$$

Case 4

The case in which optical power losses in the spectroscopic analysis portion 3 and the connector 6 of the optical probe 2 are present and an power loss at optical fiber in the optical probe 2 is also present, in other words, the case in which 0<η<1 and 0<α<1, will be described.

In this case, a total Raman scattering intensity ST4 detected by the spectroscopic measurement portion 12 is expressed by Expression (11) below.

$$Sab = \quad (11)$$
$$ST4(\lambda) = (1+2\gamma)\alpha^2\eta^2 P\sigma_1 + (L_1+L_2\alpha^2+2\gamma\alpha^2 L)\eta^2 P\sigma_g = \eta^2 ST3(\lambda)$$

R41F, which is the ratio of the Raman scattering intensity of the first optical member 7 and the Raman scattering intensity of a second optical member 22c, is expressed by Expression (12) below.

$$Rab = R41F(\lambda) = (1+2\gamma)\alpha^2\sigma_1/(L_1+L_2\alpha^2+2\gamma\alpha^2 L)\sigma_g \quad (12)$$

In Case 2, the Raman scattering intensity ST2 of the examination light detected by the spectroscopic measurement portion 12 decreases, with respect to the Raman scattering intensity ST1 detected by the spectroscopic measurement portion 12 in Case 1, by a factor contribution corresponding to the square of the transmission efficiency η(0<η<1). On the other hand, the Raman scattering intensity ratio R11F of the first optical member 7 and the optical fiber 4 in Case 1 and the Raman scattering intensity ratio R21F of the first optical member 7 and the optical fiber 4 in Case 2 are the same values.

Here, as an intermediate value between ST1 and ST2, it is possible to set an arbitrary threshold TS1. It is possible to set an arbitrary threshold TR1 that is lower than R11F and R21F.

The computation portion 14 compares, with the threshold TS1 and the threshold TR1 that are set in advance, the Raman scattering intensity Sab of the examination light at the arbitrary peak wavelength of the first optical member 7 and the Raman scattered light intensity ratio Rab of the first optical member 7 and the optical fiber 4.

Here, in the case in which conditions that Sab is Sab>TS1 with respect to the threshold TS1 and that Rab is Rab>TR1 with respect to the threshold TR1 are satisfied, the computation portion 14 determines that the connection between the receiving-side connector 8 and the connector 6 is normal and that the optical fiber 4 is normal.

In the case in which Sab is Sab<TS1 with respect to the threshold TS1 and the intensity ratio Rab is Rab>TR1 with respect to the threshold TR1, the computation portion 14 determines that, although the problem of large optical power loss is occurring at the connection between the receiving-side connector 8 and the connector 6, the optical fiber 4 is normal.

In Case 3, the Raman scattering intensity ST3 of the examination light detected by the spectroscopic measurement portion 12 decreases with respect to the total Raman scattering intensity ST1 detected by the spectroscopic measurement portion 12 in Case 1, and, furthermore, the Raman scattering intensity ratio R31F of the first optical member 7 and the optical fiber 4 also decreases as compared with R11F (and R21F).

In Case 4, the Raman scattering intensity ST4 of the examination light detected by the spectroscopic measurement portion 12 additionally decreases by a factor contribution corresponding to the square of the transmission efficiency η(0<η<1) with respect to the Raman scattering intensity ST3 detected by the spectroscopic measurement portion 12 in Case 3. On the other hand, the Raman scattering intensity ratio R41F of the first optical member 7 and the optical fiber 4 is the same value as R31F.

In Case 3 and Case 4, the Raman scattering intensity Sab of the examination light decreases, and the Raman scattering intensity ratio Rab of the first optical member 7 and the optical fiber 4 also decreases. Therefore, when the optical power loss in the optical fiber 4 and the optical power loss in the connector 6 are in the prescribed conditions, R11F and R31F are measured in advance, and an arbitrary threshold TR2 (TR2<TR1) that is lower than the threshold TR1 is set between values of R11F and R31F.

Accordingly, it is possible to distinguish optical power losses in accordance with the situations, assuming that, a state in which the condition Rab>TR1 is satisfied regarding the Raman scattering intensity ratio Rab of the first optical member 7 and the optical fiber 4 corresponds to Case 1 (both the connector 6 and the optical fiber 4 are normal) or Case 2 (optical power loss is occurring in the connector 6 and no optical power loss is occurring in the optical fiber 4), and that a state in which the condition Rab<TR2 is satisfied corresponds to Case 3 (although no optical power loss is occurring in the connector 6, optical power loss is occurring in the optical fiber 4) or Case 4 (optical power loss is occurring in the connector 6 and optical power loss is also occurring in the optical fiber 4).

In Case 4, because the Raman scattering intensity Sab of the examination light further decreases as compared with Case 3, it is possible to distinguish a state in Case 4 and a state in Case 3 on the basis of the Raman scattering intensity by setting an appropriate threshold TS2 between the values of ST3 and ST4.

As a result of setting the thresholds in this way, the computation portion 14 determines that, although the connection between the receiving-side connector 8 and the connector 6 is normal, the problem of large optical power loss is occurring in the optical fiber 4, if the conditions that the Raman scattering intensity Sab of the examination light is Sab>TS2 with respect to the above-described threshold TS2 and the Raman scattering intensity ratio Rab is Rab<TR2 with respect to the threshold TR2 are satisfied.

The computation portion 14 determines that the problem of large optical power loss is occurring at the connection between the receiving-side connector 8 and the connector 6 and the problem of large optical power loss is also occurring in the optical fiber 4, if the conditions that the Raman scattering intensity Sab of the examination light is Sab<TS2 with respect to the threshold TS2 and the Raman scattering intensity ratio Rab is Rab<TR2 with respect to the threshold TR2 are satisfied.

Here, a flow of steps from the examination to the diagnosis performed in a spectroscopic analysis method employing the spectroscopic analysis apparatus 1 according to the first embodiment of the present invention will be described below with reference to the drawings.

Figure 6:
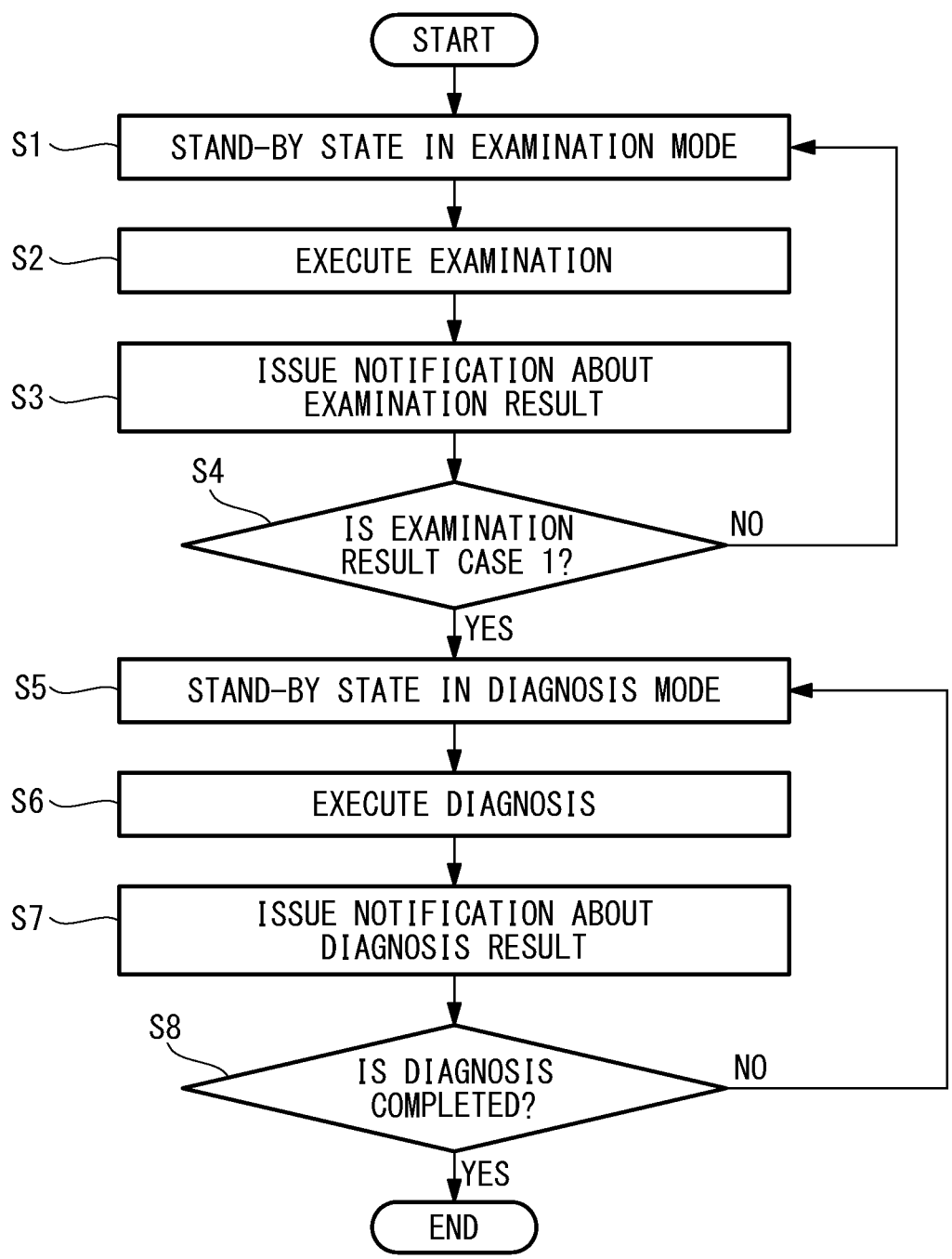
FIG. 6 is a diagram showing a flow from examination in the examination mode to diagnosis in the diagnosis mode, employing the spectroscopic analysis apparatus in FIG. 1.

When the operator turns on the spectroscopic analysis apparatus 1 from the control portion 16, the spectroscopic analysis portion 3 stands by in the examination mode (step S1), as shown in FIG. 6. Then, when the instruction for an examination is input from the input apparatus of the control portion 16, the examination is executed (step S2), and, when the processing by the computation portion 14 is completed, the examination results are notified to the operator by means of a screen (light) or a sound via the display portion 15 (step S3).

After issuing the notification to the operator, whether or not the examination results of the examination mode correspond to Case 1 is determined (step S4), and the spectroscopic analysis portion 3 is switched to the diagnosis mode, if the examination results of the examination mode correspond to Case 1, in other words, if a problem is not detected. In the case in which the examination results of the examination mode correspond to Case 2 to Case 4, in other words, in the case in which some kind of problem is detected, the processing is repeated from step S1 and the stand-by state is maintained in the examination mode until the operator takes action in accordance with the instructions issued via the display portion 15. The switch to the diagnosis mode is not made unless a state in which no problem is detected in the examination results of the examination mode is achieved.

After the switch to the diagnosis mode from the examination mode is made, the spectroscopic analysis portion 3 stands by in the diagnosis mode until diagnosis instructions are input from the input apparatus of the control portion 16 (step S5). When the diagnosis instructions are input, the diagnosis is executed by radiating the illumination light onto the observation target X (step S6), and, when the processing by the computation portion 14 is completed, the diagnosis results are notified to the operator via the display portion 15 (step S7). Then, following the notification to the operator, it is determined whether or not to terminate the diagnosis (step S8), and, if the diagnosis is not terminated, the processing from step S5 is repeated, the spectroscopic analysis portion 3 stands by in the diagnosis mode again, and thus, the diagnosis is continued.

As has been described above, with the spectroscopic analysis apparatus 1 according to this embodiment, it is possible to notify medical personnel about the cause of a problem occurring when the optical probe 2 is connected to the spectroscopic analysis portion 3, and thus, there is an advantage in that, even if the medical personnel who operates the spectroscopic analysis apparatus 1 does not have detailed knowledge, he/she can deal with a problem by identifying a site of the problem in accordance with the situation of the problem, such as optical power loss is occurring in the optical probe 2, optical power loss is occurring at the connection between the optical probe 2 and the spectroscopic analysis portion 3, or optical power losses are occurring both in the optical probe 2 and at the connection between the optical probe 2 and the spectroscopic analysis portion 3. Regarding the optical element constituting the optical probe 2, there is an advantage in that it is possible to perform the examination mode without adding elements other than the optical elements required to perform the diagnosis mode.

Next, a spectroscopic analysis apparatus 20 according to a second embodiment of the present invention will be described below with reference to drawings.

In describing this embodiment, portions having the same configurations as those of the above-described spectroscopic analysis apparatus 1 according to the first embodiment will be given the same reference signs, and the descriptions thereof will be omitted.

Figure 12:
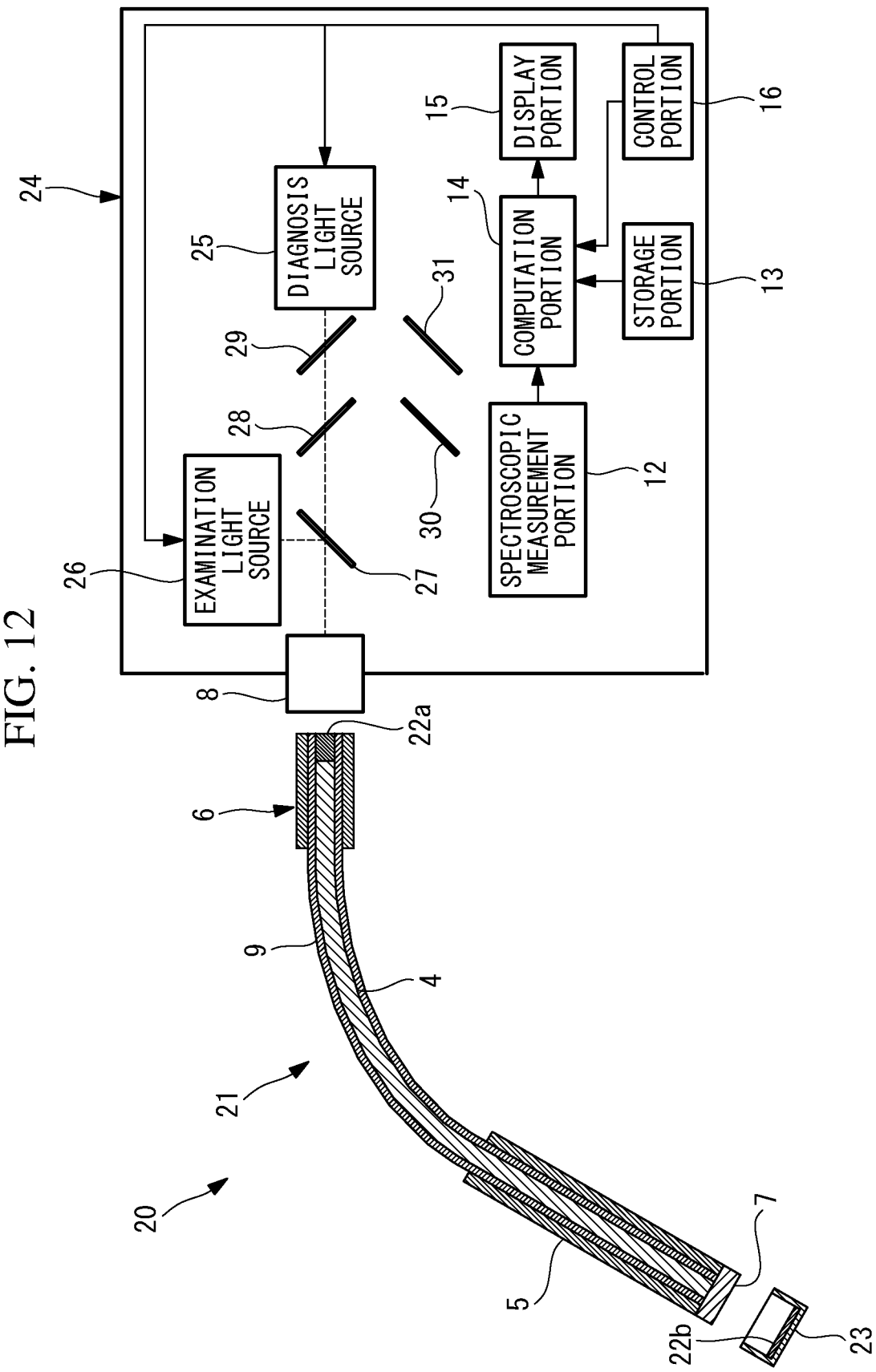
FIG. 12 is a schematic diagram showing a spectroscopic analysis apparatus according to a second embodiment of the present invention.

As shown in FIG. 12, in this embodiment, an optical probe 21 includes a second optical member (optical member) 22a formed from a phosphor that is disposed at the proximal end of the optical fiber 4 of the connector 6 and also includes a cap 23 that attaches a third optical member (optical member) 22b formed from a phosphor to the distal end of the optical probe 21 in an attachable/detachable manner. Fluorescence beams generated at the third optical member 22b and the second optical member 22a have fluorescence spectra that are different from each other and also have different wavelengths from the illumination light coming from the light source 25, 26 as well as the Raman scattered light coming from the observation target X.

The spectroscopic analysis portion 24 includes: a diagnosis light source (light source) 25 that emits diagnosis illumination light used in the diagnosis mode; and an examination light source (light source) 26 that emits examination illumination light used in the examination mode. A semiconductor laser that generates near infrared light can be employed as the diagnosis light source 25. The examination light source 26 is a light source that generates visible light or near-ultraviolet light, which is in a shorter wavelength than the light generated by the diagnosis light source 25, for example, an LED, a semiconductor laser, or a lamp. The spectroscopic analysis portion 24 includes: a first dichroic mirror 27 that reflects the examination illumination light and that allows the diagnosis illumination light, fluorescence, and Raman scattered light to pass therethrough; a second dichroic mirror 28 that allows the diagnosis illumination light and the fluorescence to pass therethrough and that reflects the Raman scattered light; a third dichroic mirror 29 that allows the diagnosis illumination light to pass therethrough and that reflects the fluorescence; a fourth dichroic mirror 30 that allows the Raman scattered light to pass therethrough and that reflects the fluorescence; and a mirror 31.

The phosphor of the second optical member 22a is a material that is optically transparent, that does not generate fluorescence in response to the photoexcitation by the diagnosis light source 25, and that generates fluorescence in response to the photoexcitation by the examination light source 26 that outputs a beam with a shorter wavelength, and, for example, fluorescent glass in which a fluorescently active element is mixed in glass can be employed. The phosphor of the third optical member 22b is a material that generates fluorescence in response to the photoexcitation by the examination light source 26, and an object in which a fluorescent substance is mixed or to which such a substance is applied or fluorescent glass can be employed.

Figure 13:
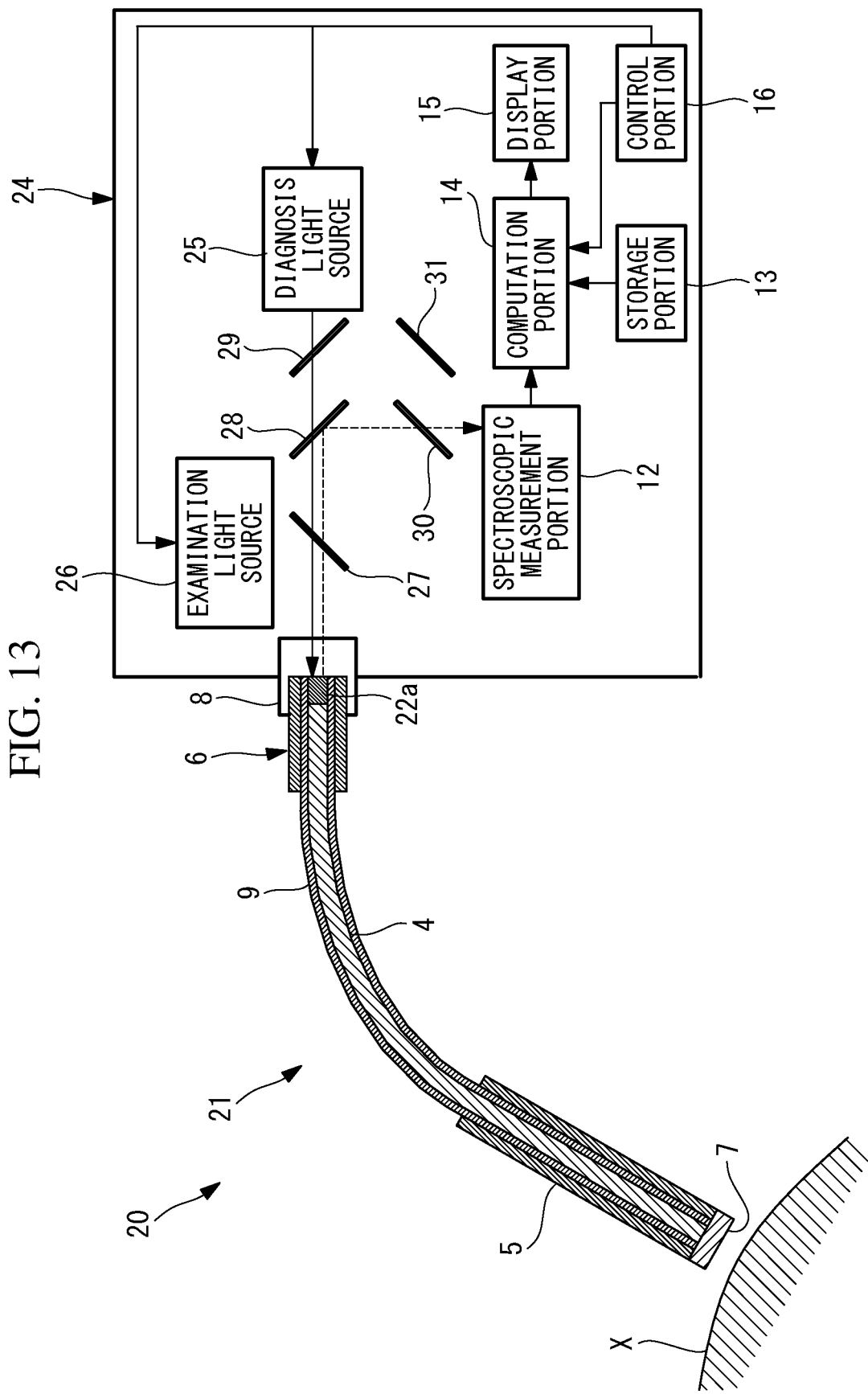
FIG. 13 is a schematic diagram for explaining an diagnosis mode of an observation target, the diagnosis mode being performed by employing the spectroscopic analysis apparatus in FIG. 12.

As shown in FIG. 13, in the diagnosis mode, the observation target X is made to face the distal end of the optical probe 21 in the state in which the cap 23 is removed, and the diagnosis illumination light is emitted from the diagnosis light source 25. At this time, via the input apparatus included in the control portion 16, the examination light source 26 is turned off or shielded so as not to influence the measurement performed in the diagnosis mode.

The diagnosis illumination light emitted from the diagnosis light source 25 enters the optical probe 21 after sequentially passing through the third dichroic mirror 29, the second dichroic mirror 28, and the first dichroic mirror 27 and is radiated onto the observation target X via the optical probe 21. The Raman scattered light generated at the observation target X passes through the first dichroic mirror 27 via the optical probe 21, is reflected by the second dichroic mirror 28, and enters the spectroscopic measurement portion 12 after passing through the fourth dichroic mirror 30. The Raman spectrum measurement in the spectroscopic analysis portion 24 and the processing in the computation portion 14 are the same as those in the first embodiment.

Figure 14:
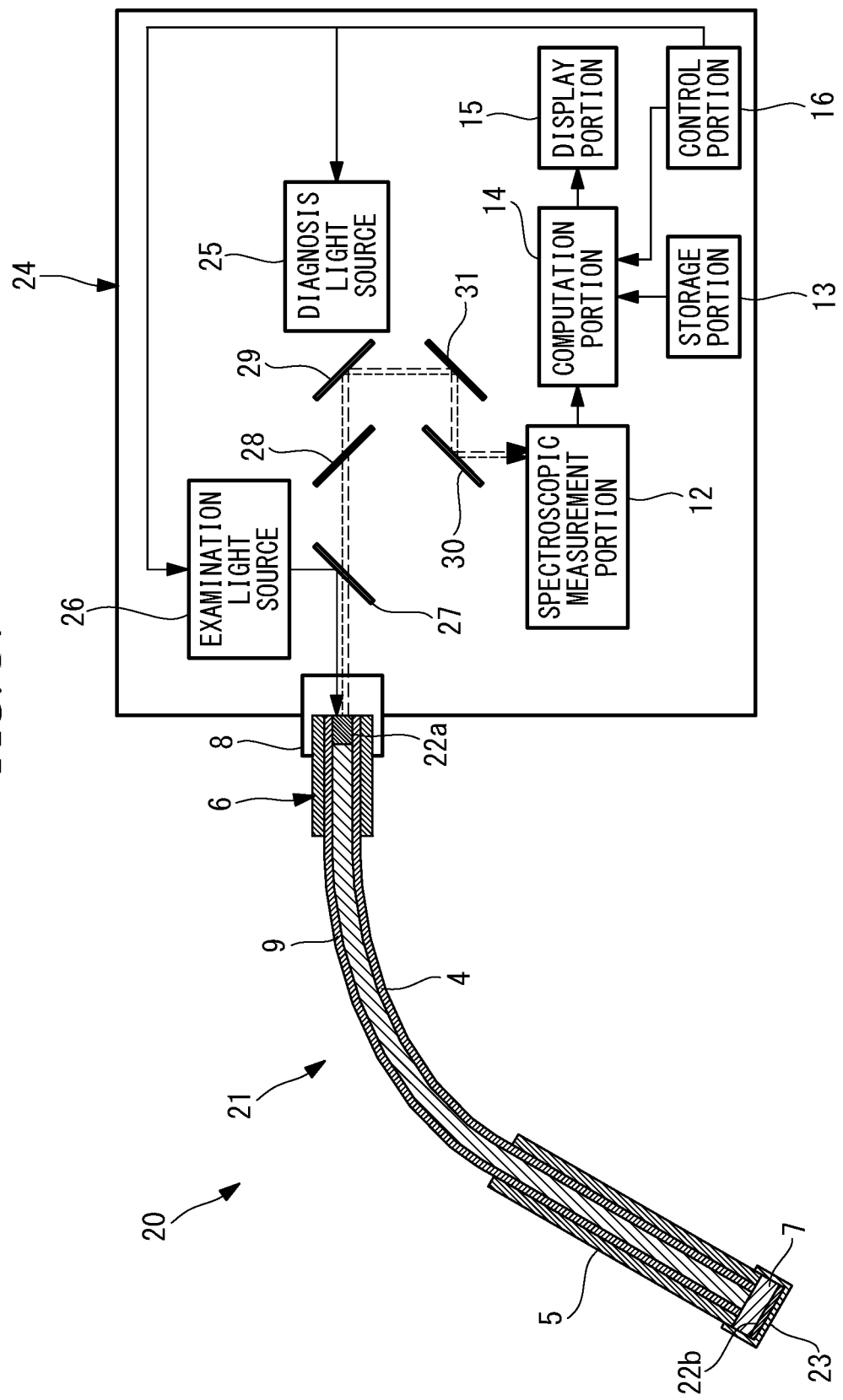
FIG. 14 is a schematic diagram for explaining an examination mode employing the spectroscopic analysis apparatus in FIG. 12.

On the other hand, as shown in FIG. 14, in the examination mode, the examination illumination light is emitted from the examination light source 26 in the state in which the cap 23 is attached to the distal end of the optical probe 21. At this time, via the input apparatus included in the control portion 16, the diagnosis light source 25 is turned off or blocked so as not to influence the examination performed in the examination mode.

The examination illumination light emitted from the examination light source 26 enters the optical probe 21 by being reflected by the first dichroic mirror 27 and is radiated onto the second optical member 22a attached to the proximal end of the connector 6 and the third optical member 22b attached to the cap 23 at the distal end of the optical probe 21. The fluorescence beam generated at the second optical member 22a and the fluorescence beam generated at the third optical member 22b enter the spectroscopic analysis portion 24, pass through the first dichroic mirror 27 and the second dichroic mirror 28, are reflected by the third dichroic mirror 29, are reflected by the mirror 31 and the fourth dichroic mirror 30, and enter the spectroscopic measurement portion 12.

In the spectroscopic measurement portion 12, as a result of detecting spectra of the fluorescence beams that have entered, an intensity A of the fluorescence beam generated at the third optical member 22b and the intensity B of the fluorescence beam generated at the second optical member 22a are respectively calculated.

In the computation portion 14, the intensity Sab and the ratio Rab are calculated by using the intensities A and B calculated in the spectroscopic measurement portion 12, and the presence/absence of the problem is determined in the same manner as in the first embodiment.

With this embodiment, the presence/absence of the problem is determined by means of the intensities of the fluorescence beams that are generated by the optical members 22a and 22b disposed at the distal end and the proximal end of the optical fiber 4 and that are easily detected because the signal intensities are higher as compared with the Raman scattering; therefore, there is an advantage in that it is possible to more easily notify information regarding the problem.

Next, a spectroscopic analysis apparatus 32 according to a third embodiment of the present invention will be described below with reference to drawings.

In describing this embodiment, portions having the same configurations as those of the above-described spectroscopic analysis apparatus 1 according to the first embodiment will be given the same reference signs and the descriptions thereof will be omitted.

Figure 15:
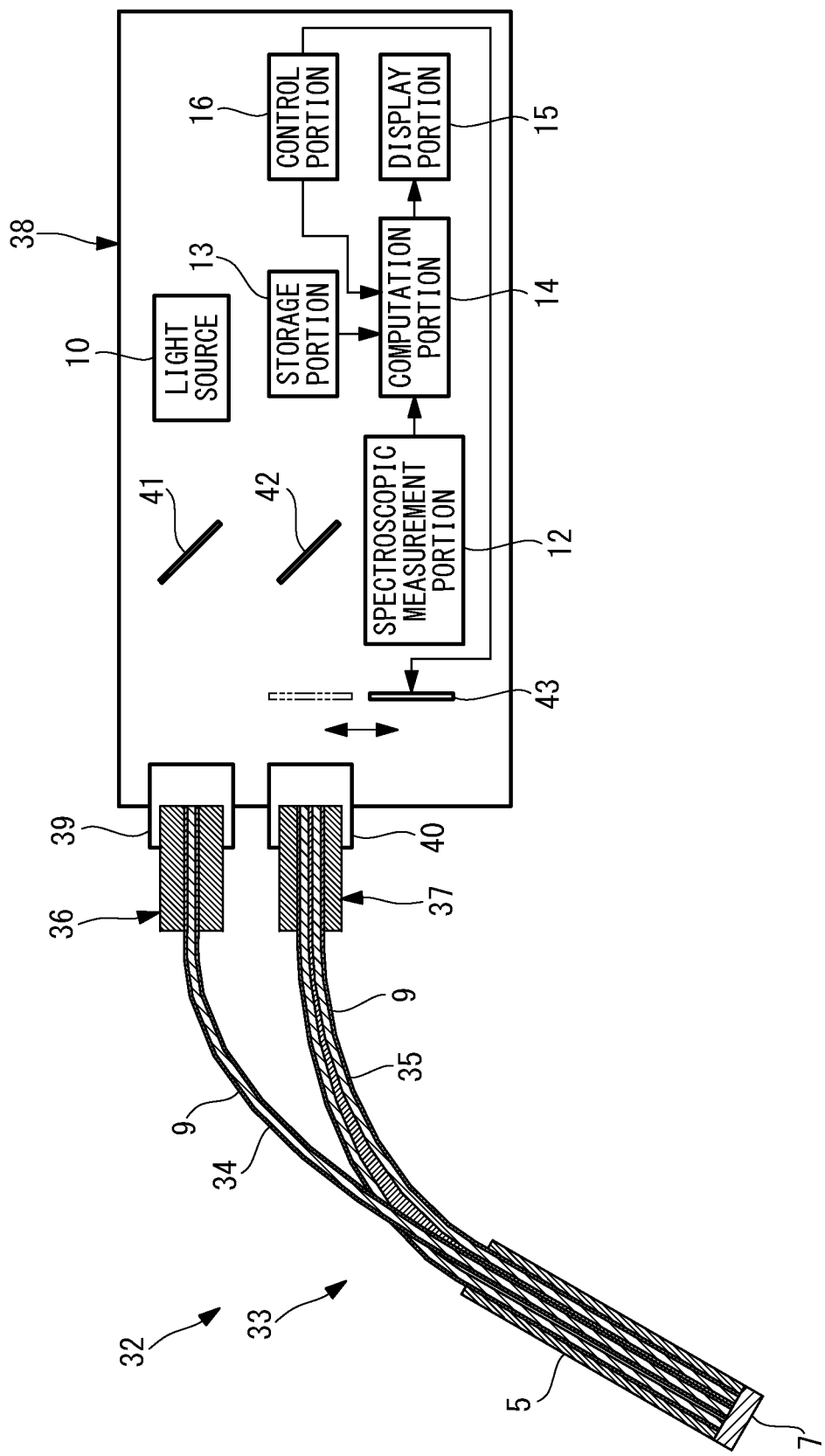
FIG. 15 is a schematic diagram showing a spectroscopic analysis apparatus according to a third embodiment of the present invention.

As shown in FIG. 15, in the spectroscopic analysis apparatus 32 according to this embodiment, an optical probe 33 separately includes an illumination fiber (optical fiber) 34 that guides the illumination light and a light collecting fiber (optical fiber) 35 that guides the return light, and separate connectors 36 and 37 are respectively connected to a proximal end of the illumination fiber 34 and a proximal end of the light collecting fiber 35.

A spectroscopic analysis portion 38 separately has a first receiving-side connector 39 to which the connector 36 of the illumination fiber 34 is connected and a second receiving-side connector 40 to which the connector 37 of the light collecting fiber 35 is connected.

The first optical member 7 at a distal end of the optical probe 33 is a material that generates Raman scattered light beams in a plurality of wavelengths in response to photoexcitation and is, for example, a sapphire crystal. In the case in which the first optical member 7 is a sapphire crystal, as a vibration mode of the sapphire crystal, three different Raman peaks occur in vicinity of Raman shift values of 420 $cm^{-1}$, 580 $cm^{-1}$, and 750 $cm^{-1}$.

Although the first optical member 7 generates the plurality of Raman peaks, of these Raman peaks, the wavelengths of the two different Raman peaks are respectively assumed to be a first peak wavelength $\lambda 1$ and a second peak wavelength $\lambda 2$ that are generated by the first optical member 7.

Here, the first peak wavelength $\lambda 1$ is a shorter wavelength than the second peak wavelength $\lambda 2$ ($\lambda 1 < \lambda 2$). In the case in which the observation target X is biological tissue, it is possible to select a longer wavelength than the second peak wavelength $\lambda 2$ as a region of interest in the Raman spectrum of the observation target X. Materials of the illumination fiber 34 and the light collecting fiber 35 are, for example, silica.

A first dichroic mirror 41 that allows the illumination light to pass therethrough and that reflects the Raman scattered light generated at the first optical member 7 and the illumination fiber 34 is disposed between the light source 10 and the first receiving-side connector 39.

A second dichroic mirror 42 that reflects, of the Raman scattered light generated at the first optical member 7 and the light collecting fiber 35, a long-wavelength component containing the second peak wavelength $\lambda 2$ and that allows a short-wavelength component containing the first peak wavelength $\lambda 1$ to pass therethrough is disposed between the spectroscopic measurement portion 12 and the second receiving-side connector 40.

An optical shutter 43 that opens/closes the optical path between the second receiving-side connector 40 and the second dichroic mirror 42 is disposed in the spectroscopic analysis portion 38. Opening/closing of the optical shutter 43 is executed by means of an electrical signal transmitted to the optical shutter 43 from the control portion 16.

Figure 16:
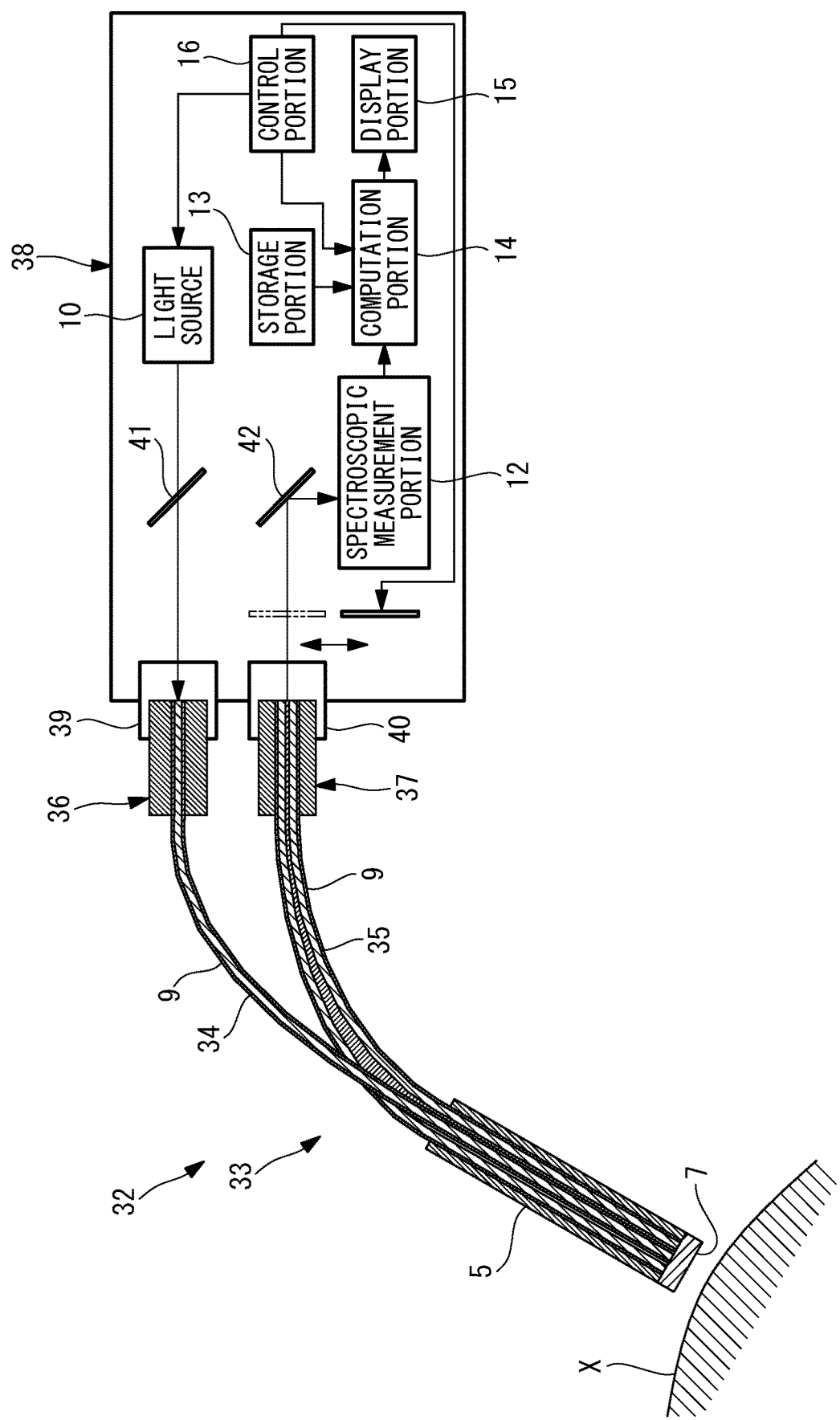
FIG. 16 is a schematic diagram for explaining a diagnosis mode of an observation target, the diagnosis mode being performed by employing the spectroscopic analysis apparatus in FIG. 15.
Figure 19:
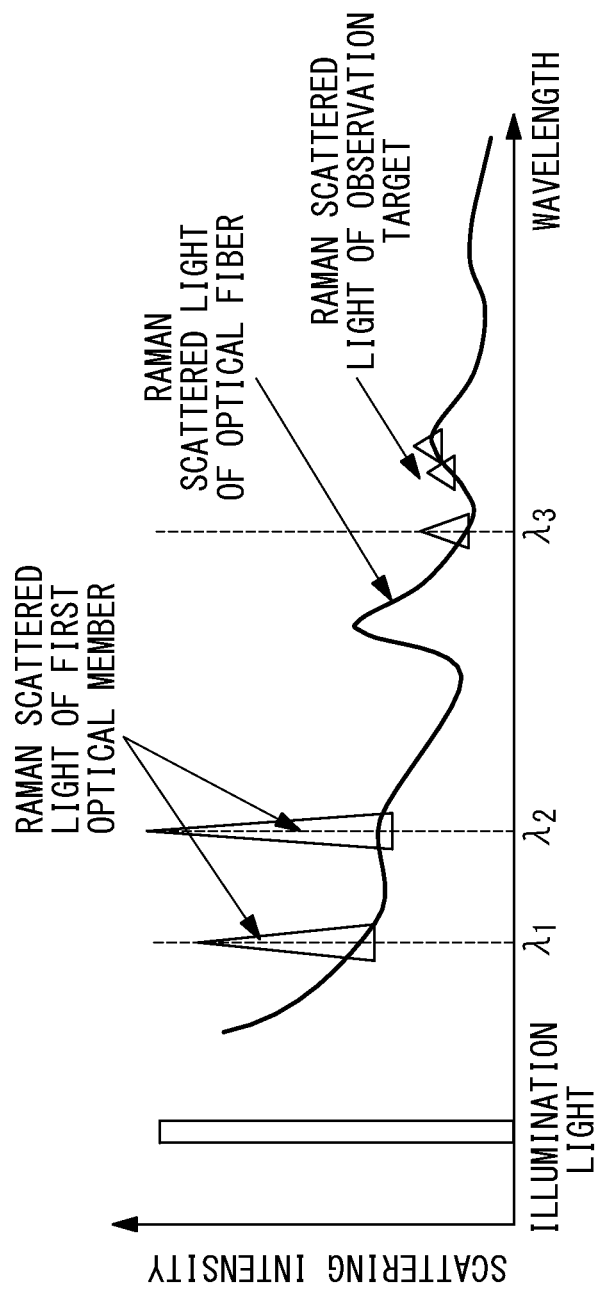
FIG. 19 is a diagram showing a spectrum of return light generated in the diagnosis mode performed by employing the spectroscopic analysis apparatus in FIG. 15.
Figure 20:
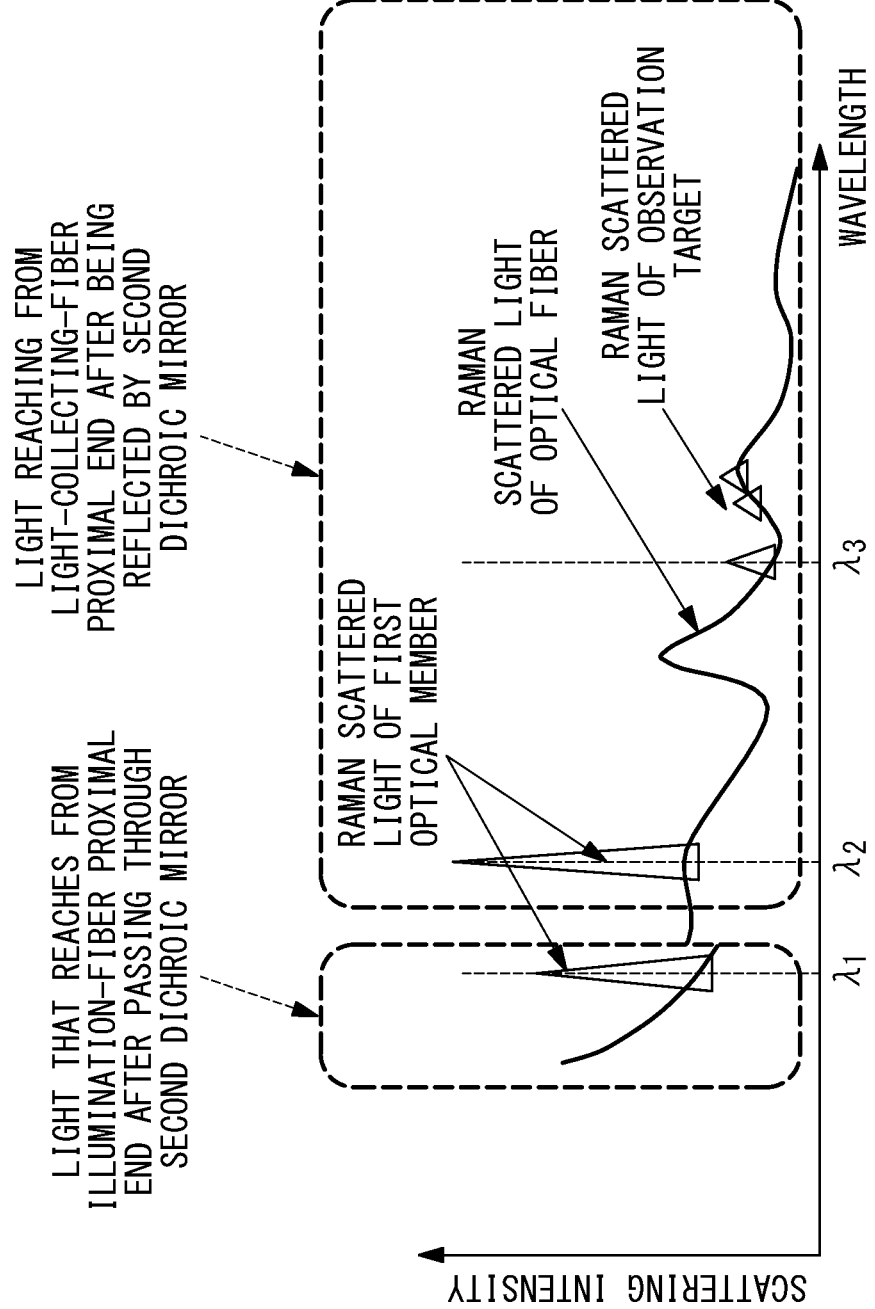
FIG. 20 is a diagram showing a spectrum of examination light detected by a spectroscopic measurement portion 12 in the diagnosis mode performed by employing the spectroscopic analysis apparatus in FIG. 15.

In the diagnosis mode, in the state in which the optical shutter 43 is open as shown in FIG. 16, the observation target X is made to face the distal end of the optical probe 33 and the illumination light is emitted from the light source 10. A spectrum of the return light generated in the diagnosis mode is as shown in FIG. 19. The illumination light emitted from the light source 10 enters the illumination fiber 34 after passing through the first dichroic mirror 41 and is radiated onto the observation target X via the illumination fiber 34. The Raman scattered light generated at the observation target X is reflected by the second dichroic mirror 42 via the light collecting fiber 35 and enters the spectroscopic measurement portion 12. As shown in FIG. 20, a spectrum of the examination light detected by the spectroscopic measurement portion 12 contains not only the component that enters after being reflected by the second dichroic mirror via the light collecting fiber 35 but also the component that enters after passing through the second dichroic mirror 42 via the illumination fiber 34; however, there is no influence on the diagnosis of the observation target X, because only the shorter wavelength range than 23 is contained. The Raman spectrum measurement in the spectroscopic measurement portion 12 and the processing in the computation portion 14 are the same as those in the first embodiment.

Figure 21:
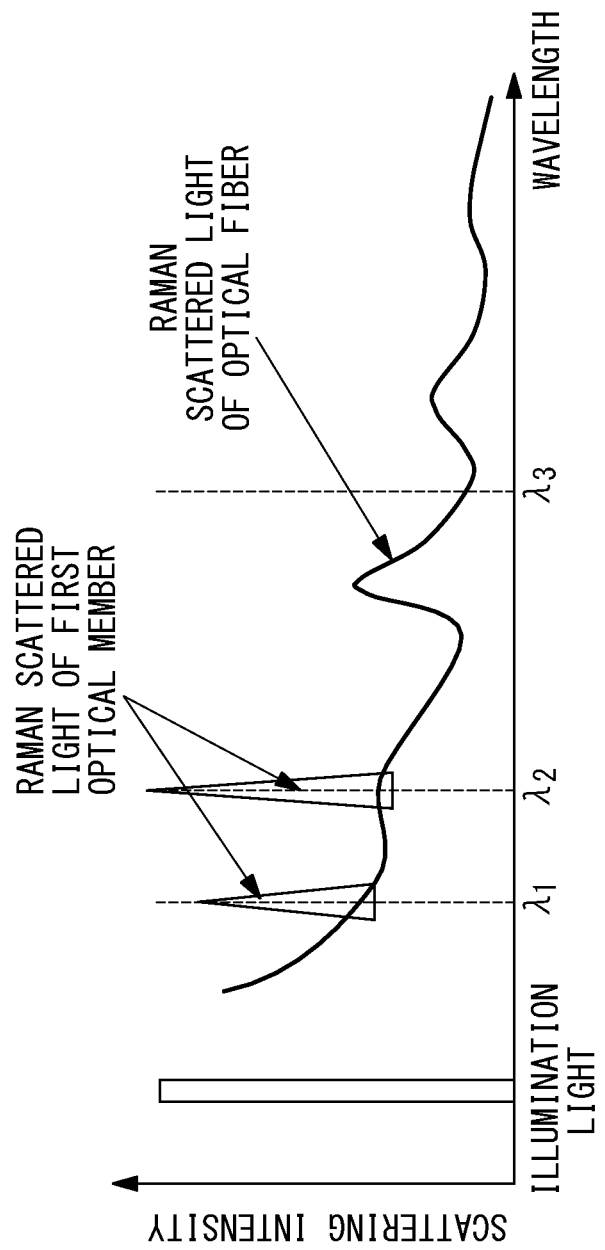
FIG. 21 is a diagram showing a spectrum of return light generated in the examination mode performed by employing the spectroscopic analysis apparatus in FIG. 15.

On the other hand, in the examination mode, the examination of the optical path containing the illumination fiber 34 and the examination of the optical path containing the light collecting fiber 35 are performed separately. A spectrum of the return light at the proximal ends of the illumination fiber 34 and the light collecting fiber 35 in the examination mode is as shown in FIG. 21.

Figure 17:
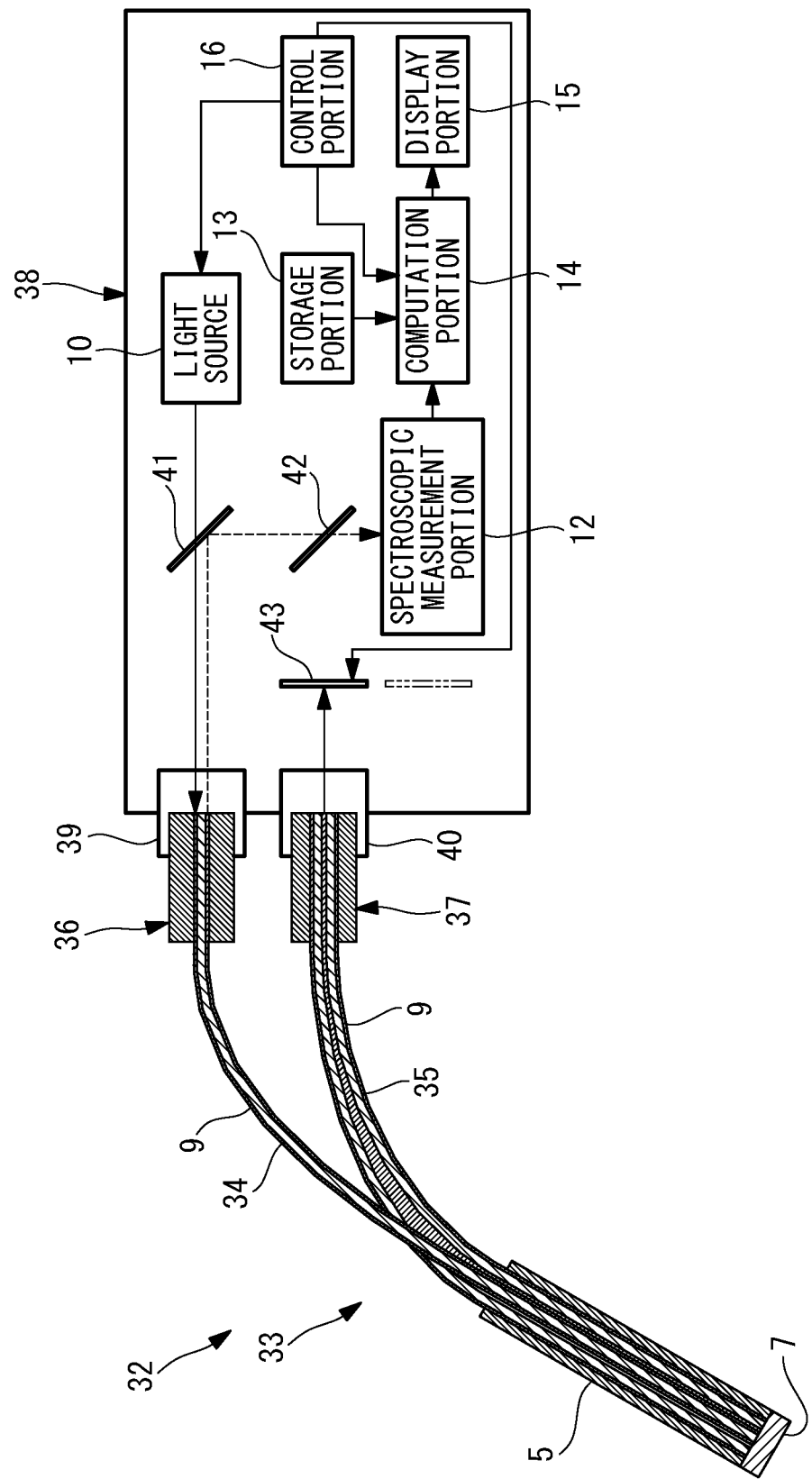
FIG. 17 is a schematic diagram for explaining an examination mode of an optical path containing an illumination fiber, the examination mode being performed by employing the spectroscopic analysis apparatus in FIG. 15.

In the examination of the optical path containing the illumination fiber 34, as shown in FIG. 17, the illumination light is emitted from the light source 10 in the state in which the optical path between the second receiving-side connector 40 and the second dichroic mirror 42 is shut off by actuating the optical shutter 43.

Figure 22:
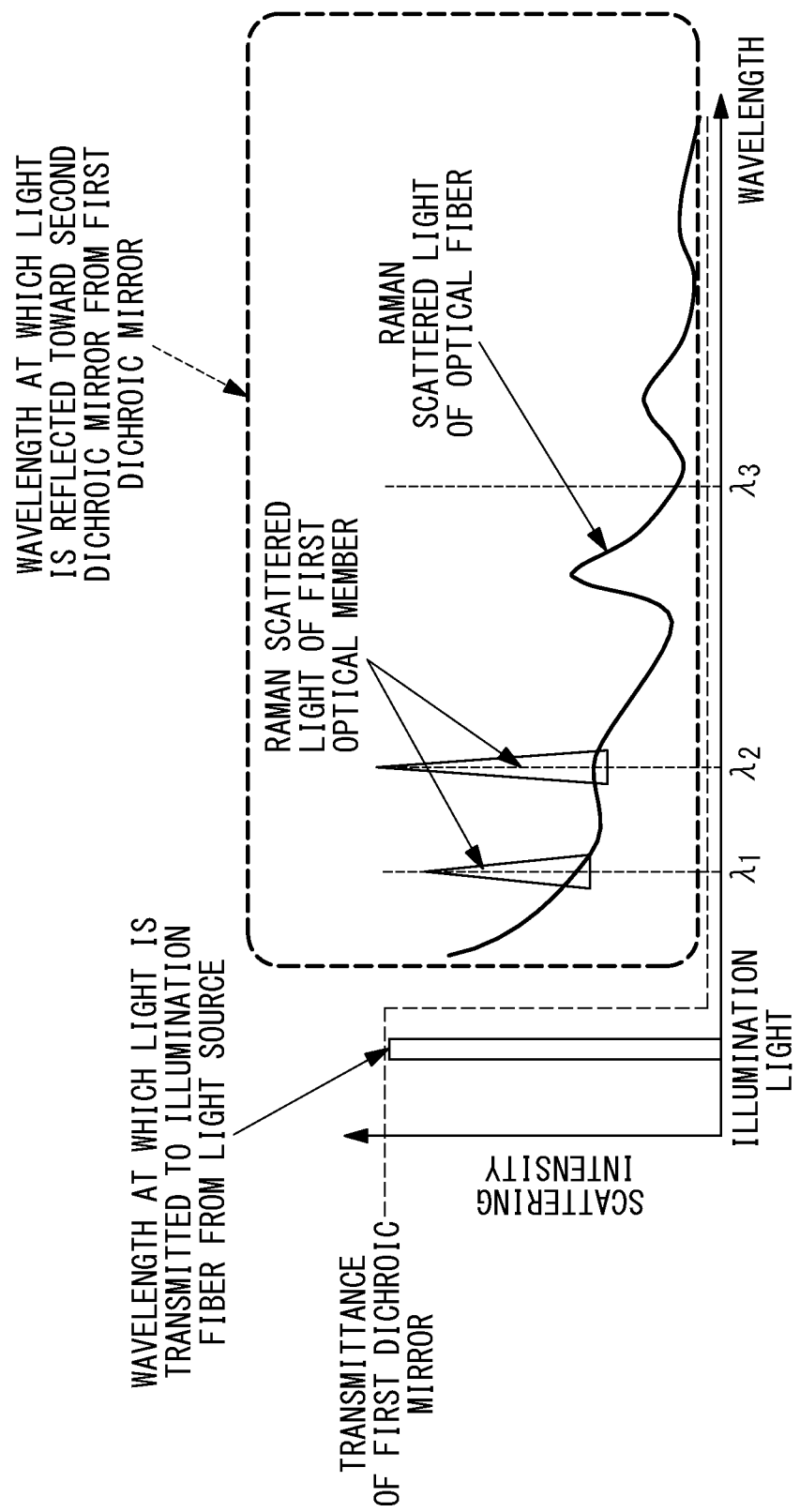
FIG. 22 is a diagram showing the relationship among wavelengths at a first dichroic mirror in the examination mode performed by employing the spectroscopic analysis apparatus in FIG. 15.

The illumination light emitted from the light source 10 enters the illumination fiber 34 after passing through the first dichroic mirror 41, and the Raman scattered light is generated inside the illumination fiber 34 and at the first optical member 7. The Raman scattered light enters the spectroscopic analysis portion 38 via the first receiving-side connector 39 and is reflected by the first dichroic mirror 41. The relationship among the wavelengths at the first dichroic mirror 41 at this time is as shown in FIG. 22.

Figure 23:
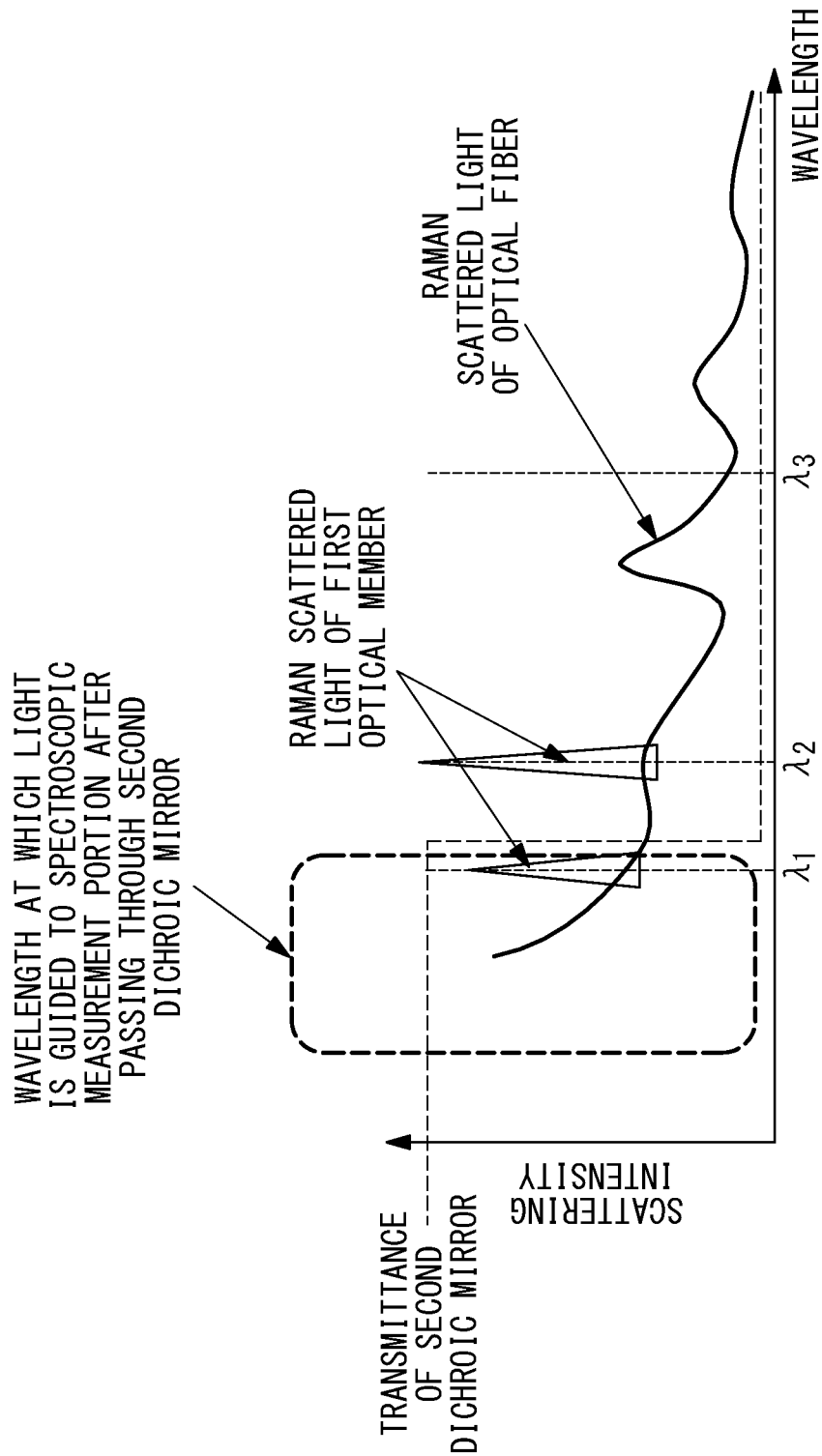
FIG. 23 is a diagram showing the relationship among wavelengths at a second dichroic mirror in the examination mode of the optical path containing the illumination fiber, the examination mode being performed by employing the spectroscopic analysis apparatus FIG. 15.
Figure 24:
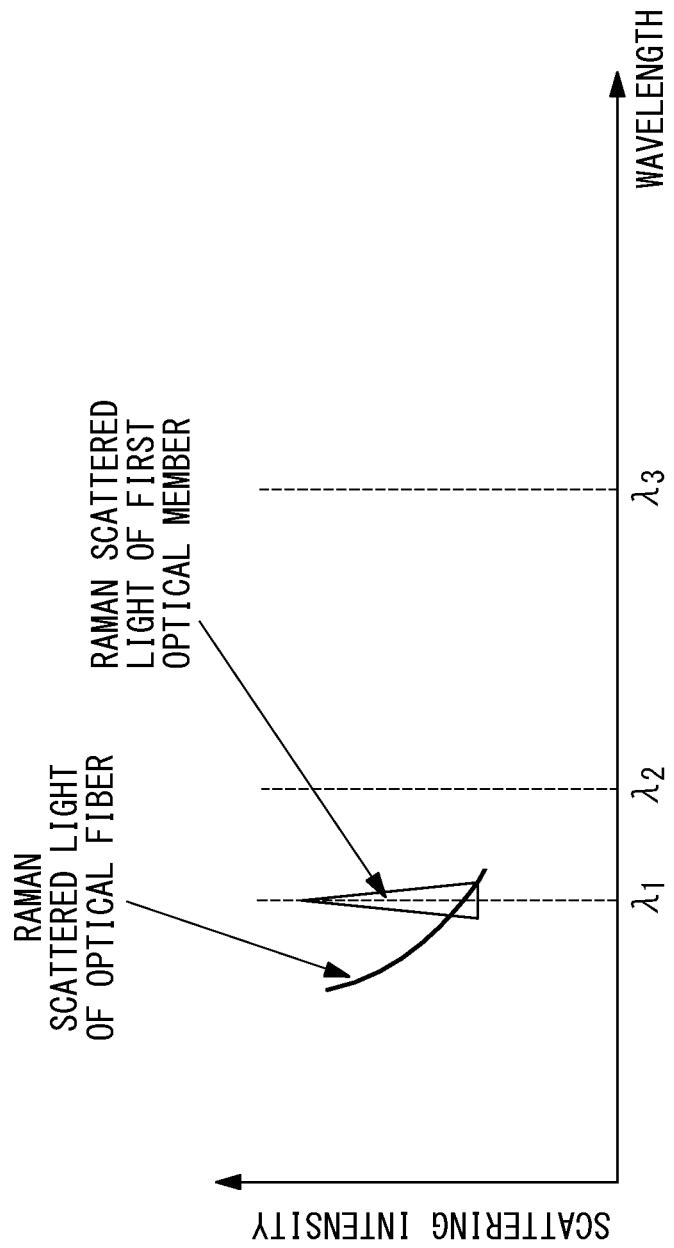
FIG. 24 is a diagram showing a spectrum of examination light detected in the examination mode of the optical path containing the illumination fiber, the examination mode being performed by employing the spectroscopic analysis apparatus in FIG. 15.

Next, of the Raman scattered light of the optical fiber 4 of the illumination fiber 34 and the first optical member 7, the short-wavelength component containing the first peak wavelength $\lambda 1$ is made to pass through the second dichroic mirror 42 and enters the spectroscopic measurement portion 12. The relationship among the wavelengths at the second dichroic mirror 42 at this time is as shown in FIG. 23, and the spectrum of the examination light detected by the spectroscopic measurement portion 12 is as shown in FIG. 24.

In the examination of the optical path containing the illumination fiber 34, the computation portion 14: determines, from the input Raman spectrum of the examination light, the examination-light intensity Sab ($=A+B$) of the Raman scattered light of the first optical member 7 at the first peak wavelength $\lambda 1$; identifies the intensity B of the Raman scattered light of the illumination fiber 34 at the above-described wavelength from the Raman spectrum of the illumination fiber 34 stored in the storage portion 13; and calculates the Rab ($=A/B$) of the intensity A of the Raman scattered light of the first optical member 7 at the first peak wavelength 21 and the Raman scattering intensity B of the illumination fiber 34.

The computation portion 14 compares the intensity Sab with the threshold TS1 and the threshold TS2 stored in the storage portion 13 and compares the ratio Rab with the threshold TR1 and the threshold TR2 stored in the storage portion 13, and thus, the computation portion 14 determines the presence/absence of a problem in accordance with the comparison results. Because the details of this method is the same as that in the first embodiment, the description thereof will be omitted.

Figure 18:
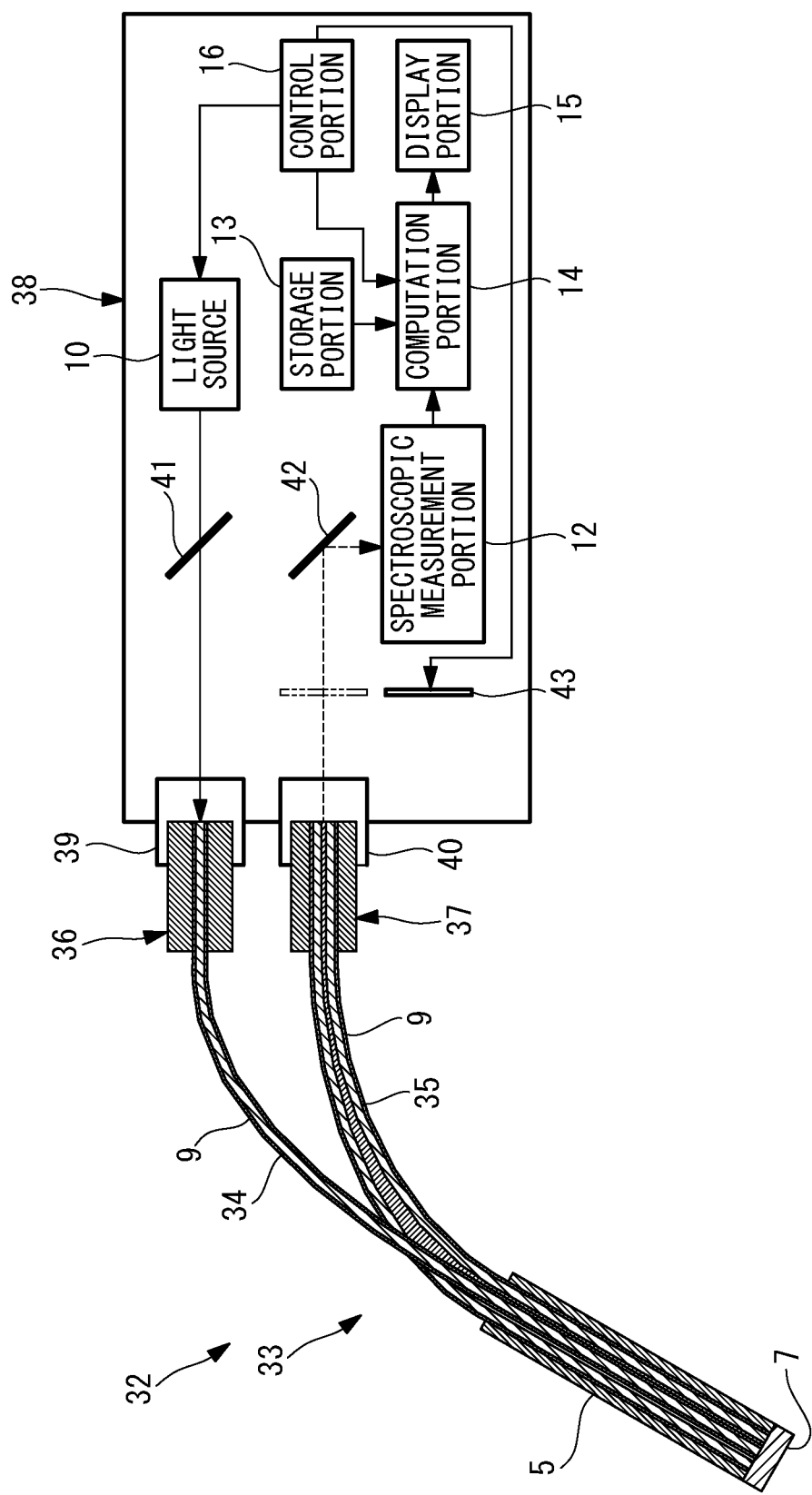
FIG. 18 is a schematic diagram for explaining an examination mode of an optical path containing a light collecting fiber, the examination mode being performed by employing the spectroscopic analysis apparatus in FIG. 15.

In the examination of the optical path containing the light collecting fiber 35, as shown in FIG. 18, the illumination light is emitted from the light source 10 in the state in which the optical path between the second receiving-side connector 40 and the second dichroic mirror 42 is opened by actuating the optical shutter 43.

Figure 25:
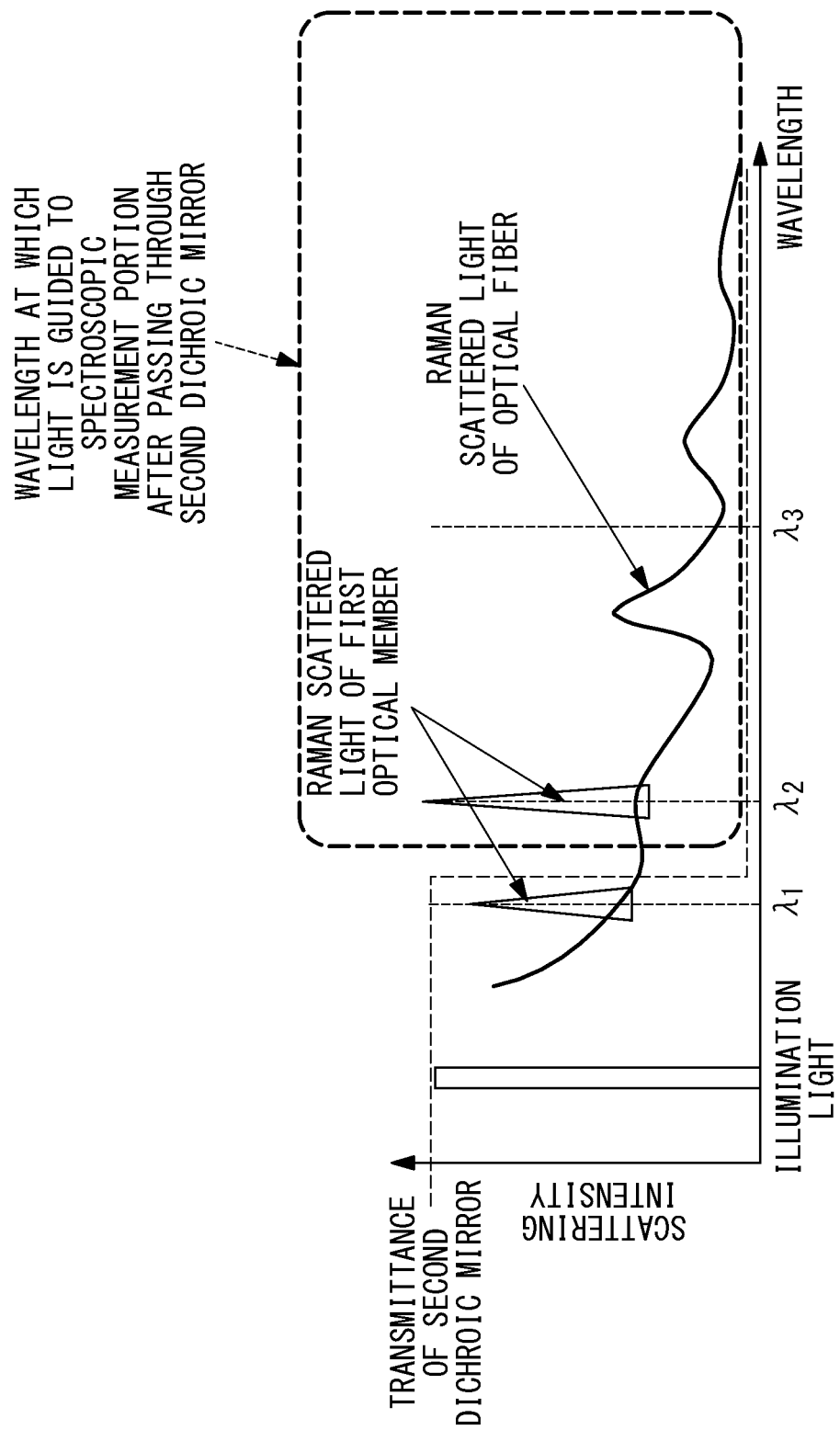
FIG. 25 is a diagram showing the relationship among wavelengths at the second dichroic mirror in the examination mode of the optical path containing the light collecting fiber, the examination mode being performed by employing the spectroscopic analysis apparatus in FIG. 15.
Figure 26:
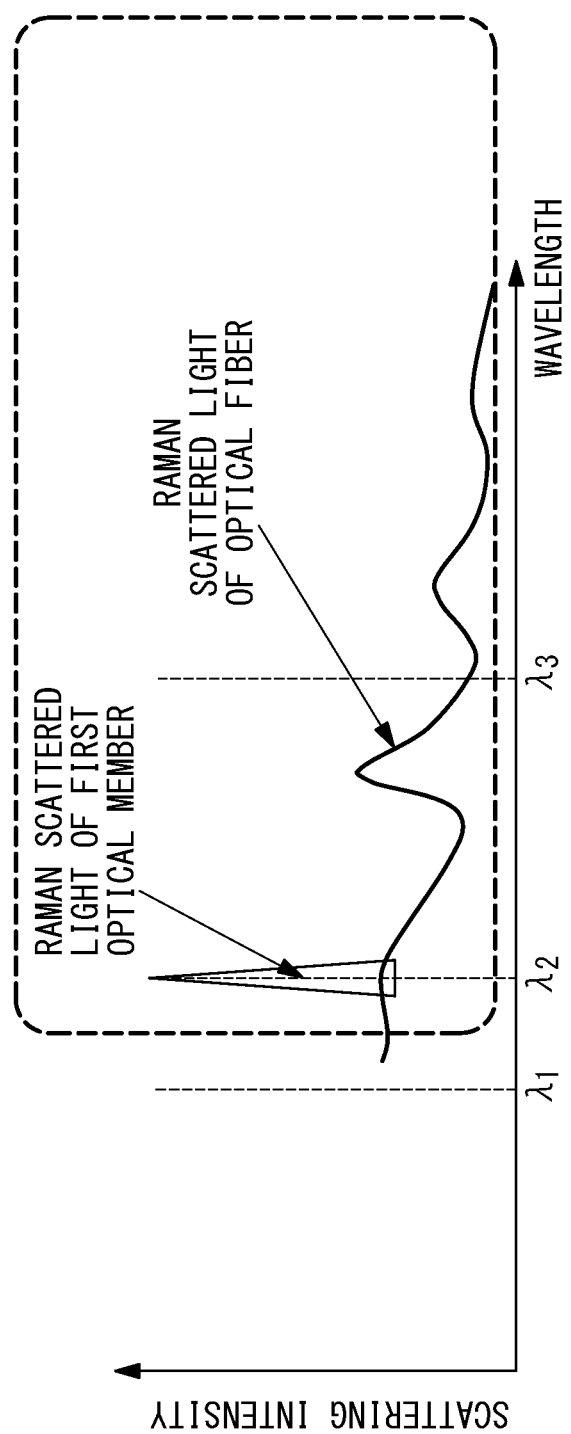
FIG. 26 is a diagram showing a spectrum derived from the return light coming from the optical path containing the light collecting fiber in the examination light detected in the examination mode of the optical path containing the light collecting fiber, the examination mode being performed by employing the spectroscopic analysis apparatus in FIG. 15.

The illumination light emitted from the light source 10 enters the illumination fiber 34 after passing through the first dichroic mirror 41 and the Raman scattered light beams generated inside the illumination fiber 34, inside the light collecting fiber 35, and at the first optical member 7 enter the spectroscopic analysis portion 38 via the second receiving-side connector 40. Of this Raman scattering light, the wavelength component that is longer wavelength than the first peak wavelength $\lambda 1$ of the first optical member 7 and that encompasses the second peak wavelength $\lambda 2$ is reflected by the second dichroic mirror 42 and enters the spectroscopic measurement portion 12. The relationships among the wavelengths at the second dichroic mirror 42 at this time is as shown in FIG. 25, and the spectrum of the examination light that enters the spectroscopic measurement portion 12 is as shown in FIG. 26.

Figure 27:
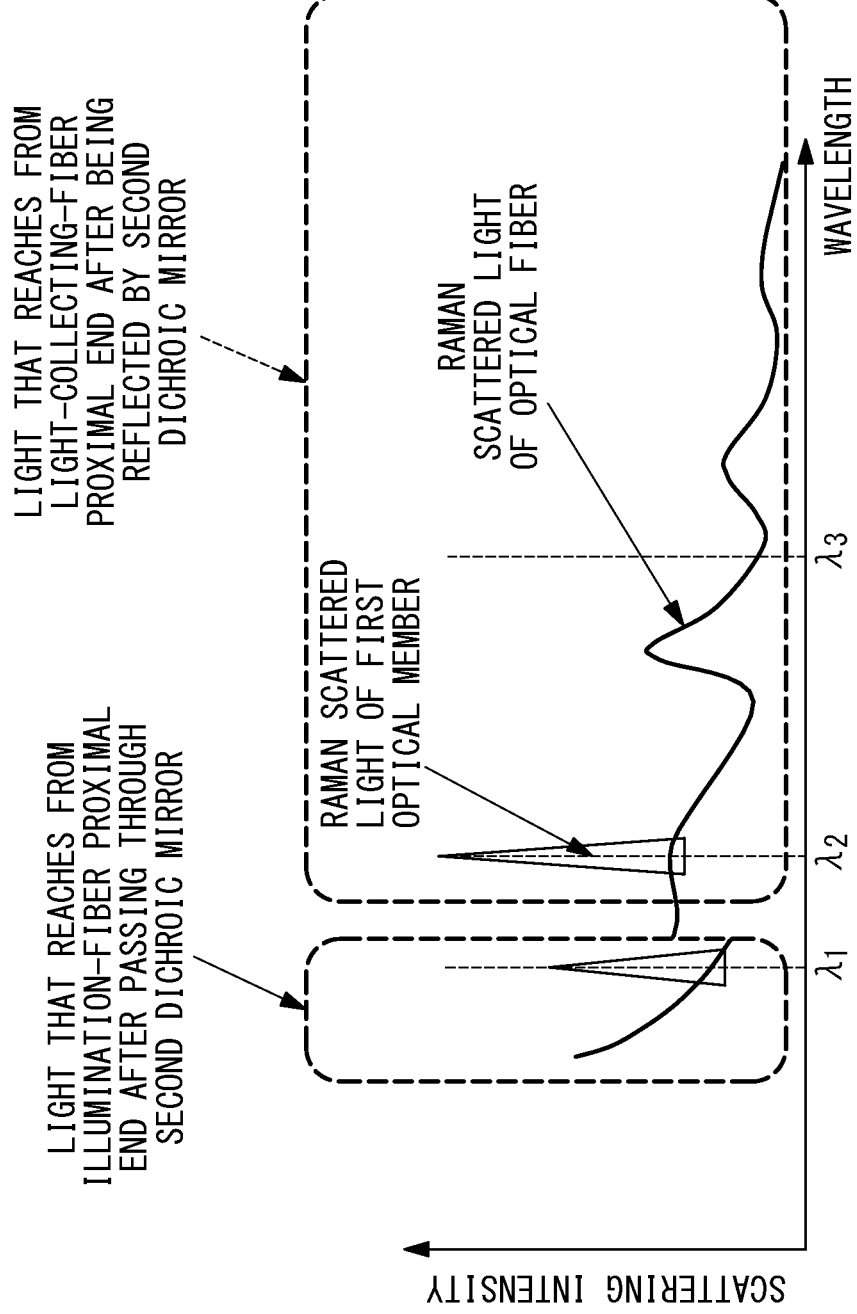
FIG. 27 is a diagram showing a spectrum of the examination light detected in the examination mode of the optical path containing the light collecting fiber, the examination mode being performed by employing the spectroscopic analysis apparatus in FIG. 15.

The spectroscopic measurement portion 12 detects the Raman spectrum of the entered light. As shown in FIG. 27, the spectrum detected in the spectroscopic measurement portion 12 contains not only the component that enters after being reflected by the second dichroic mirror via the light collecting fiber 35 but also the component that enters after passing through the second dichroic mirror 42 via the illumination fiber 34; however, there is no influence on the examination of the optical path containing the light collecting fiber 35, because only the shorter wavelength range than 22 is contained. The examination light detected by the spectroscopic measurement portion 12 contains the Raman scattered light generated at the illumination fiber 34, the Raman scattered light generated at the first optical member 7, and the Raman scattered light generated at the light collecting fiber 35 due to the illumination light reflected by the first optical member 7.

The detected Raman spectrum is input to the computation portion 14.

In the examination of the optical path containing the light collecting fiber 35, the computation portion 14: determines, from the input Raman spectrum of the examination light, the examination-light intensity Sab (=A+B) of the Raman scattered light of the first optical member 7 at the second peak wavelength λ2; identifies the intensity B of the Raman scattered light of the illumination fiber 34 and the light collecting fiber 35 at the above-described wavelength from the spectra of the Raman scattered light of the illumination fiber 34 and the light collecting fiber 35 stored in the storage portion 13; and calculates the ratio Rab (=A/B) of the intensity A of the Raman scattered light of the first optical member 7 and the intensity B of the Raman scattered light of the illumination fiber 34 and the light collecting fiber 35.

The computation portion 14 compares the intensity Sab with the threshold TS1 and the threshold TS2 stored in the storage portion 13, also compares the ratio Rab with the threshold TR1 and the threshold TR2 stored in the storage portion 13, and thus, the computation portion 14 determines the presence/absence of a problem in accordance with the comparison results, as described below. The display portion 15 displays the determination results of the computation portion 14.

In the case in which Sab>TS1 and Rab>TR1, the computation portion 14 determines that optical power losses at the connection between the first receiving-side connector 39 and the connector 36 and the connection between the second receiving-side connector 40 and the connector 37 as well as optical power losses in the illumination fiber 34 and the light collecting fiber 35 are in an allowable range, and thus, the computation portion 14 determines that there is no problem.

In the case in which Sab<TS1 and Rab>TR1, the computation portion 14 determines that, although the problem of large optical power loss is occurring at the connection between the first receiving-side connector 39 and the connector 36 as well as at the connection between the second receiving-side connector 40 and the connector 37, the illumination fiber 34 and the light collecting fiber 35 are normal.

In the case in which TS2<Sab<TS1 and Rab<TR1, the computation portion 14 determines that the connection between the first receiving-side connector 39 and the connector 36 and the connection between the second receiving-side connector 40 and the connector 37 are normal and the problem of large optical power loss is occurring in the illumination fiber 34 and the light collecting fiber 35.

In the case in which Sab<TS2 and Rab<TR1, the computation portion 14 determines that the problem of large optical power loss is occurring at the connection between the first receiving-side connector 39 and the connector 36 as well as at the connection between the second receiving-side connector 40 and the connector 37 and the problem of large optical power loss is also occurring in the illumination fiber 34 and the light collecting fiber 35.

With this embodiment, as a result of separately performing the examination of the optical path that passes through the illumination fiber 34 and the examination of the optical path that passes through the light collecting fiber 35 without changing the optical path of the illumination light, even in the case in which the illumination fiber 34, which is the illumination optical path of the optical probe 33, and the light collecting fiber 35, which is the light-collecting optical path, are optical paths that are independent of each other, there is an advantage in that it is possible to determine in which one of the illumination fiber 34 and the light collecting fiber 35 optical power loss in the optical probe 33 is occurring.

There is an advantage in that it is possible to switch between the case of examining a problem in the optical path that passes through the illumination fiber 34 and the case of examining a problem in the optical path that passes through the light collecting fiber 35 without moving the dichroic mirror 41, 42 by varying the peak wavelength of the Raman scattered light to be used.

Next, a spectroscopic analysis apparatus 44 according to a fourth embodiment of the present invention will be described below with reference to drawings.

In describing this embodiment, portions having the same configurations as those of the above-described spectroscopic analysis apparatus 32 according to the third embodiment will be given the same reference signs and the descriptions thereof will be omitted.

Figure 28:
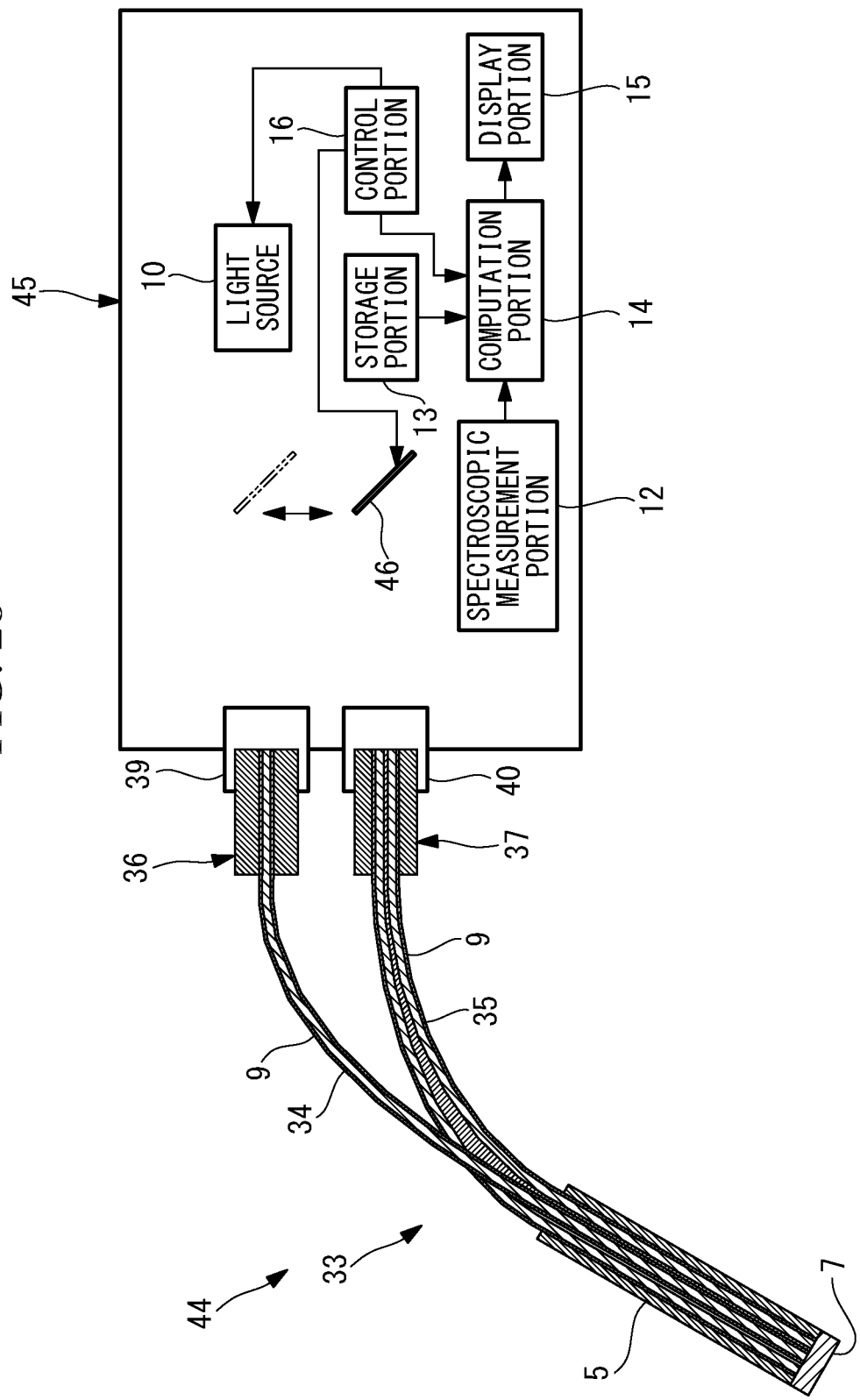
FIG. 28 is a diagram showing a spectroscopic analysis apparatus according to a fourth embodiment of the present invention.

As shown in FIG. 28, in the spectroscopic analysis apparatus according to this embodiment, a spectroscopic analysis portion 45 includes a dichroic mirror 46 that can be selectively disposed between the light source 10 and the first receiving-side connector 39 or between the second receiving-side connector 40 and the spectroscopic measurement portion 12.

Figure 29:
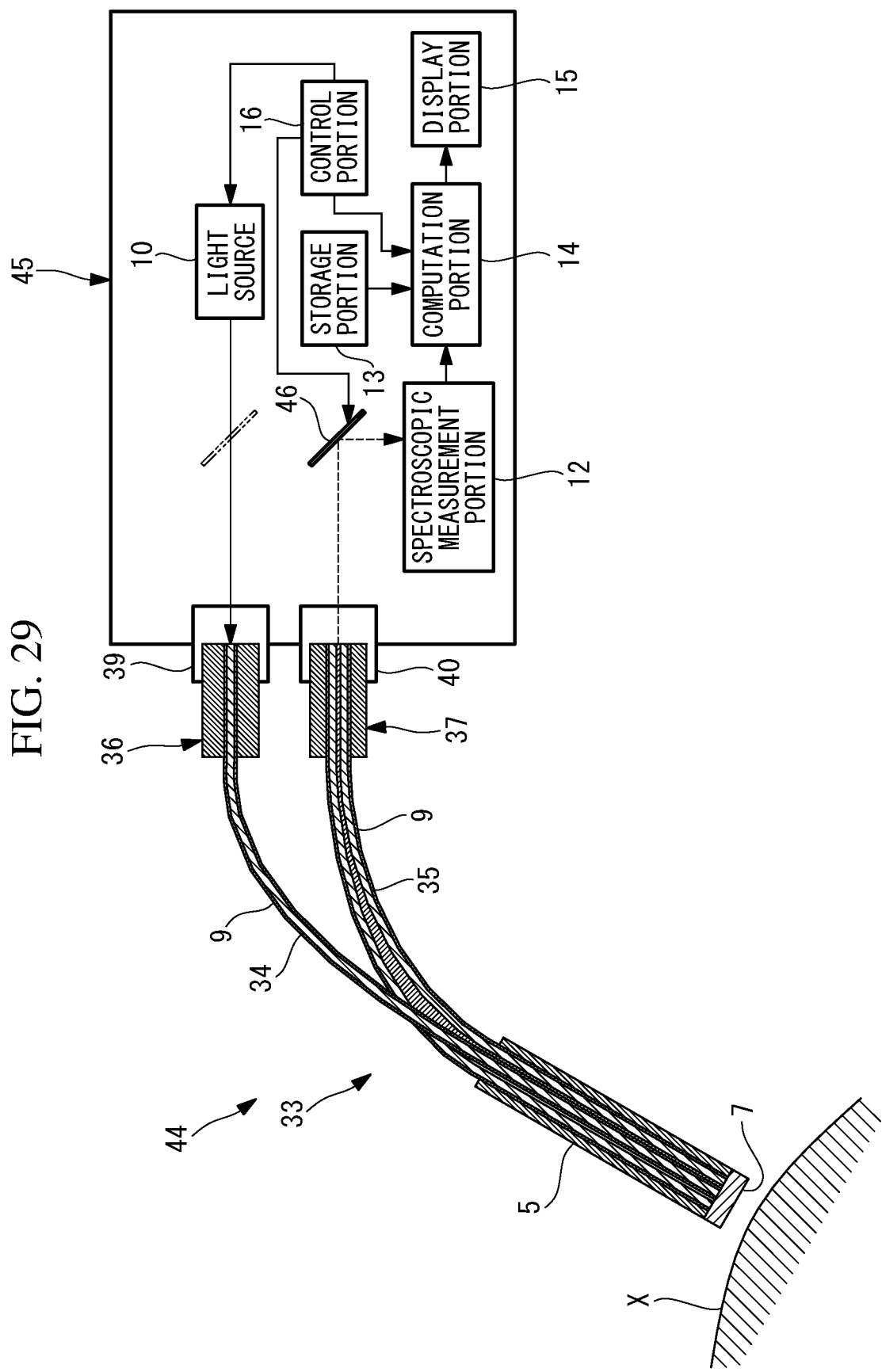
FIG. 29 is a schematic diagram for explaining a diagnosis mode of an observation target, the diagnosis mode being performed by employing the spectroscopic analysis apparatus in FIG. 28.

In the diagnosis mode, in the state in which the dichroic mirror 46 is disposed between the second receiving-side connector 40 and the spectroscopic measurement portion 12 as shown in FIG. 29, the observation target X is made to face the distal end of the optical probe 33 and the illumination light is emitted from the light source 10. The illumination light emitted from the light source 10 enters the illumination fiber 34 and is radiated onto the observation target X via the illumination fiber 34. The Raman scattered light generated at the observation target X is reflected by the dichroic mirror 46 via the light collecting fiber 35 and enters the spectroscopic measurement portion 12. The Raman spectrum measurement in the spectroscopic measurement portion 12 and the processing in the computation portion 14 are the same as those in the first embodiment.

On the other hand, in the examination mode, the examination of the optical path containing the illumination fiber 34 and the examination of the optical path containing the light collecting fiber 35 are performed separately.

Figure 30:
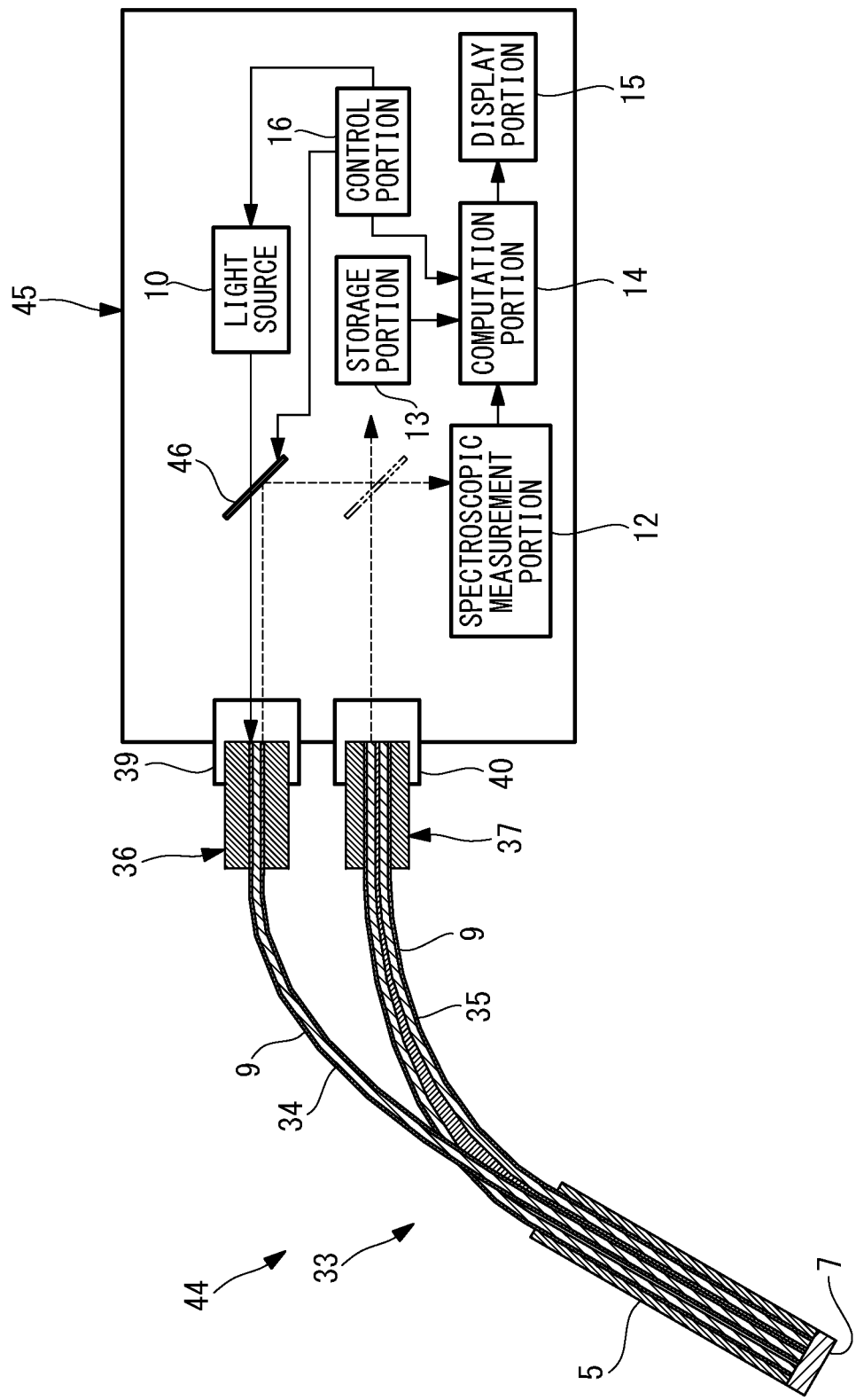
FIG. 30 is a schematic diagram for explaining an examination mode of an optical path containing an illumination fiber, the examination mode being performed by employing the spectroscopic analysis apparatus in FIG. 28.

As shown in FIG. 30, in the examination of the optical path containing the illumination fiber 34, the illumination light is emitted from the light source 10 in the state in which the dichroic mirror 46 is moved to the position between the light source 10 and the first receiving-side connector 39.

The illumination light emitted from the light source 10 enters the illumination fiber 34 after passing through the dichroic mirror 46, the Raman scattered light occurred, at the first peak wavelength, inside the illumination fiber 34 and at the first optical member 7 enters the spectroscopic analysis portion 45 via the first receiving-side connector 39, and enters the spectroscopic measurement portion 12 by being reflected by the dichroic mirror 46. The Raman spectrum measurement in the spectroscopic measurement portion 12 and the processing in the computation portion 14 are the same as those in the first embodiment.

Figure 31:
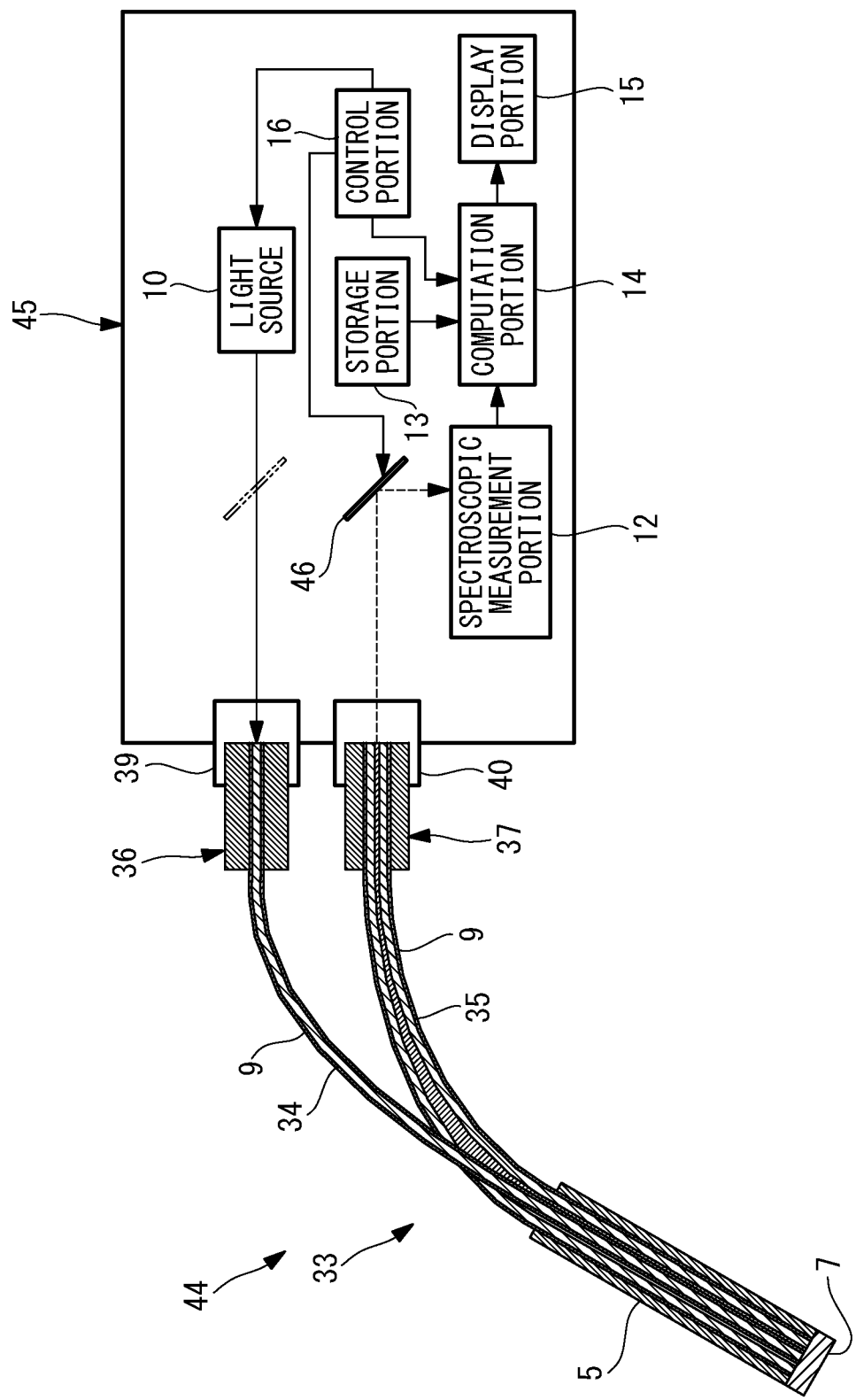
FIG. 31 is a schematic diagram for explaining an examination mode of an optical path containing a light collecting fiber, the examination mode being performed by employing the spectroscopic analysis apparatus in FIG. 28.

As shown in FIG. 31, in the examination of the optical path containing the light collecting fiber 35, the illumination light is emitted from the light source 10 in the state in which the dichroic mirror 46 is moved to the position between the second receiving-side connector 40 and the spectroscopic measurement portion 12.

The illumination light emitted from the light source 10 enters the illumination fiber 34 and the Raman scattered light generated, at the second peak wavelength, inside the illumination fiber 34, inside the light collecting fiber 35, and at the first optical member 7 enters the spectroscopic analysis portion 45 via the second receiving-side connector 40 and enters the spectroscopic measurement portion 12 by being reflected by the dichroic mirror 46.

The spectroscopic measurement portion 12 measures the Raman spectrum of the entered light. The examination light that enters the spectroscopic measurement portion 12 contains the Raman scattered light generated inside the illumination fiber 34, the Raman scattered light generated at the first optical member 7, the illumination light reflected by the first optical member 7, and the Raman scattered light generated inside the light collecting fiber 35 due to the reflected illumination light.

The measured Raman spectrum is input to the computation portion 14.

The computation portion 14 determines, from the input Raman spectrum of the examination light, the examination-light intensity Sab (=A+B) of the Raman scattered light of the first optical member 7 at the second peak wavelength; identifies the intensity B of the Raman scattered light of the illumination fiber 34 and the light collecting fiber 35, at the above-described wavelength, from the spectra of the Raman scattered light of the illumination fiber 34 and the light collecting fiber 35 stored in the storage portion 13; and calculates the ratio Rab (=A/B) of the intensity A of the Raman scattered light of the first optical member 7 and the intensity B of the Raman scattered light of the illumination fiber 34 and the light collecting fiber 35.

The computation portion 14 compares the intensity Sab with the threshold TS1 and the threshold TS2 stored in the storage portion 13, also compares the ratio Rab with the threshold TR1 and the threshold TR2 stored in the storage portion 13, and thus, the computation portion 14 determines the presence/absence of a problem in accordance with the comparison results, as described below. The display portion 15 displays the determination results of the computation portion 14. The determination method is the same as that of the third embodiment.

With this embodiment, as a result of separately performing the examination of the optical path that passes through the light collecting fiber 35 without changing the optical path of the illumination light even in the case in which the illumination fiber 34, which is the illumination optical path of the optical probe 33, and the light collecting fiber 35, which is the light-collecting optical path, are optical paths that are independent of each other, there is an advantage in that it is possible to determine in which one of the illumination fiber 34 and the light collecting fiber 35 optical power loss in the optical probe 33 is occurring. There is an advantage in that it is also possible to separately perform examinations by using a single dichroic mirror in the case in which a greater number of optical paths that are independent of each other are involved.

Next, a spectroscopic analysis apparatus 55 according to a fifth embodiment of the present invention will be described below with reference to drawings.

In describing this embodiment, portions having the same configurations as those of the above-described spectroscopic analysis apparatus 1 according to the first embodiment will be given the same reference signs and the descriptions thereof will be omitted.

Figure 32:
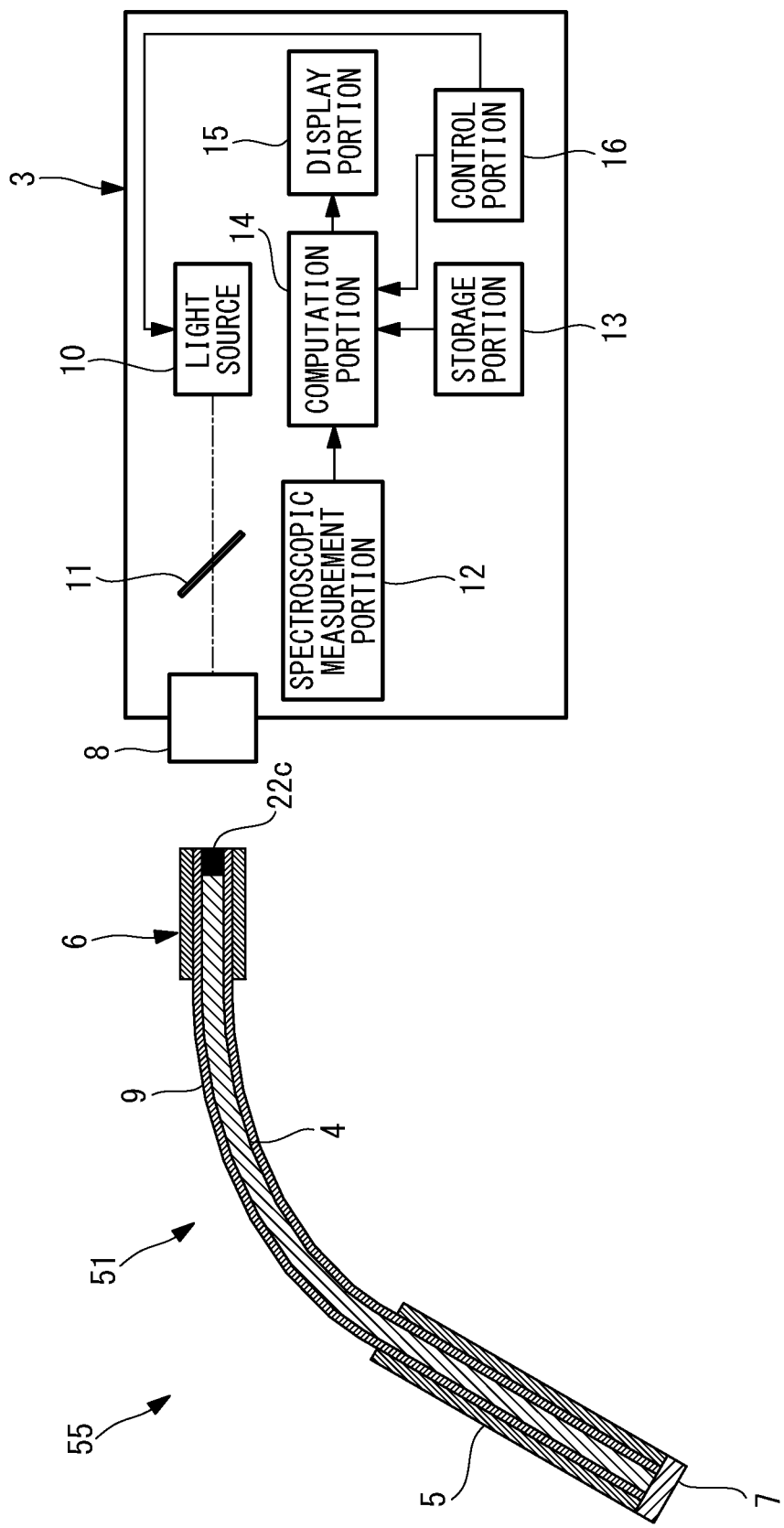
FIG. 32 is a schematic diagram showing a spectroscopic analysis apparatus according to a fifth embodiment of the present invention.

As shown in FIG. 32, in this embodiment, an optical probe 51 includes the first optical member (optical member) 7 that is disposed at the position facing the distal end of the optical fiber 4 and the second optical member (optical member) 22c that is disposed at the proximal end of the optical fiber 4 of the connector 6.

The first optical member 7 and the second optical member 22c are formed of optically transparent materials that generate Raman spectra that are different from each other. As such materials, for example, a sapphire can be employed as the first optical member 7, a sapphire can be employed as the second optical member 22c, and silica can be employed as the optical fiber 4. In this case, in the sapphire of the second optical member 22c and the sapphire of the first optical member 7, crystal surfaces that are different from each other need to serve as incident surfaces for the illumination light. Alternatively, the first optical member 7 and the second optical member 22c may respectively be of a sapphire and a plastic such as a fluoroplastic and the optical fiber 4 may be of silica. Alternatively, the first optical member 7 and the second optical member 22c may respectively be of a sapphire and a fused silica and the optical fiber 4 may be of a plastic such as a fluoroplastic.

Figure 33:
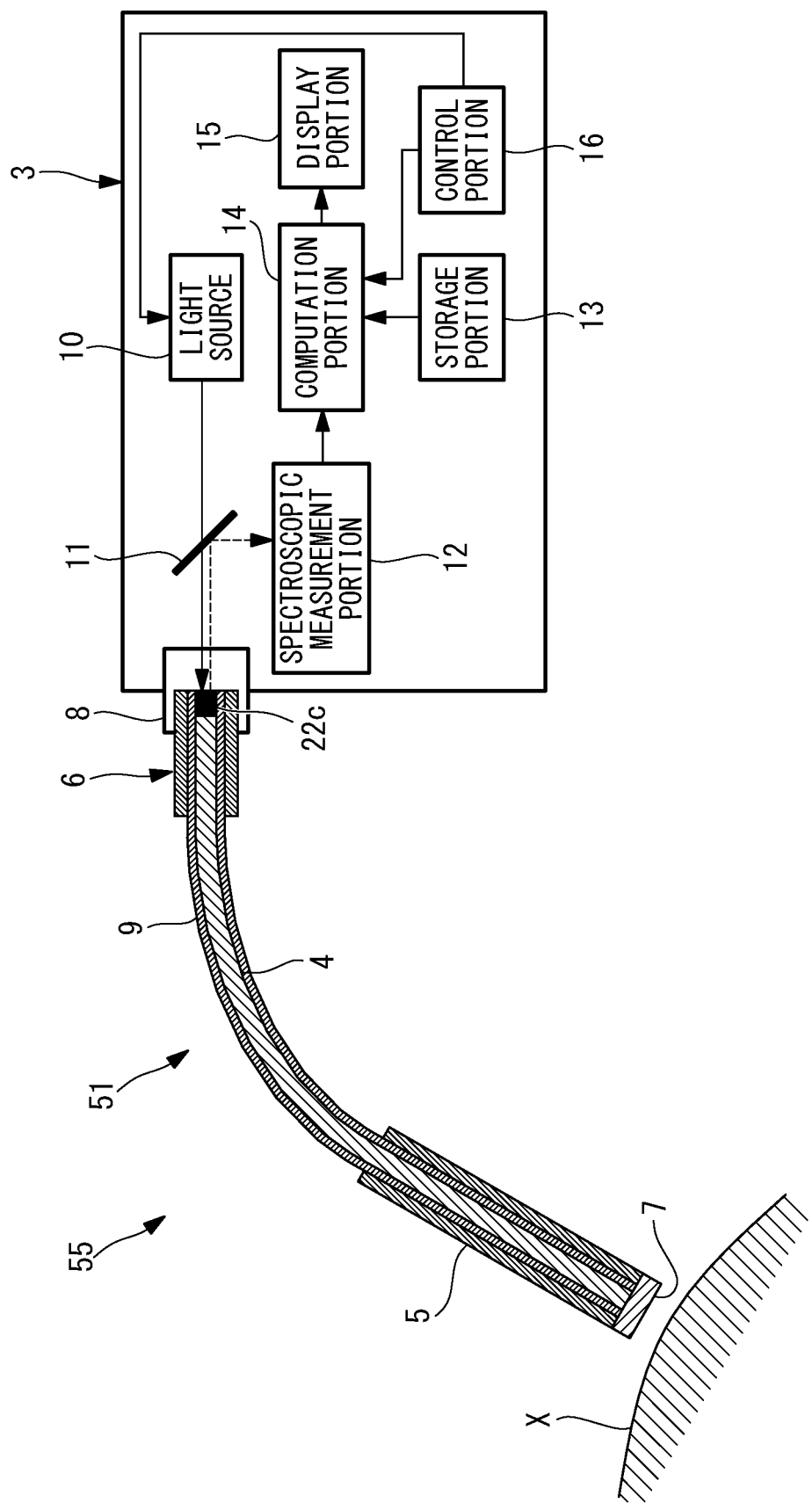
FIG. 33 is a schematic diagram for explaining a diagnosis mode of an observation target, the diagnosis mode being performed by employing the spectroscopic analysis apparatus in FIG. 32.

As shown in FIG. 33, the optical probe 51 includes the optical fiber 4, the first optical member 7, and the second optical member 22c, and, when the illumination light radiated from the light source 10 enters the optical probe 51, Raman scattered light beams having different spectral shapes are radiated from the optical fiber 4, the first optical member 7, and the second optical member 22c. In other words, when the illumination light is emitted from the light source 10 after connecting the connector 6 of the optical probe 51 to the receiving-side connector 8 of the spectroscopic analysis portion 3 and disposing the observation target X at the distal end of the optical probe 51, the illumination light is radiated onto the observation target X via the optical probe 51.

Figure 34:
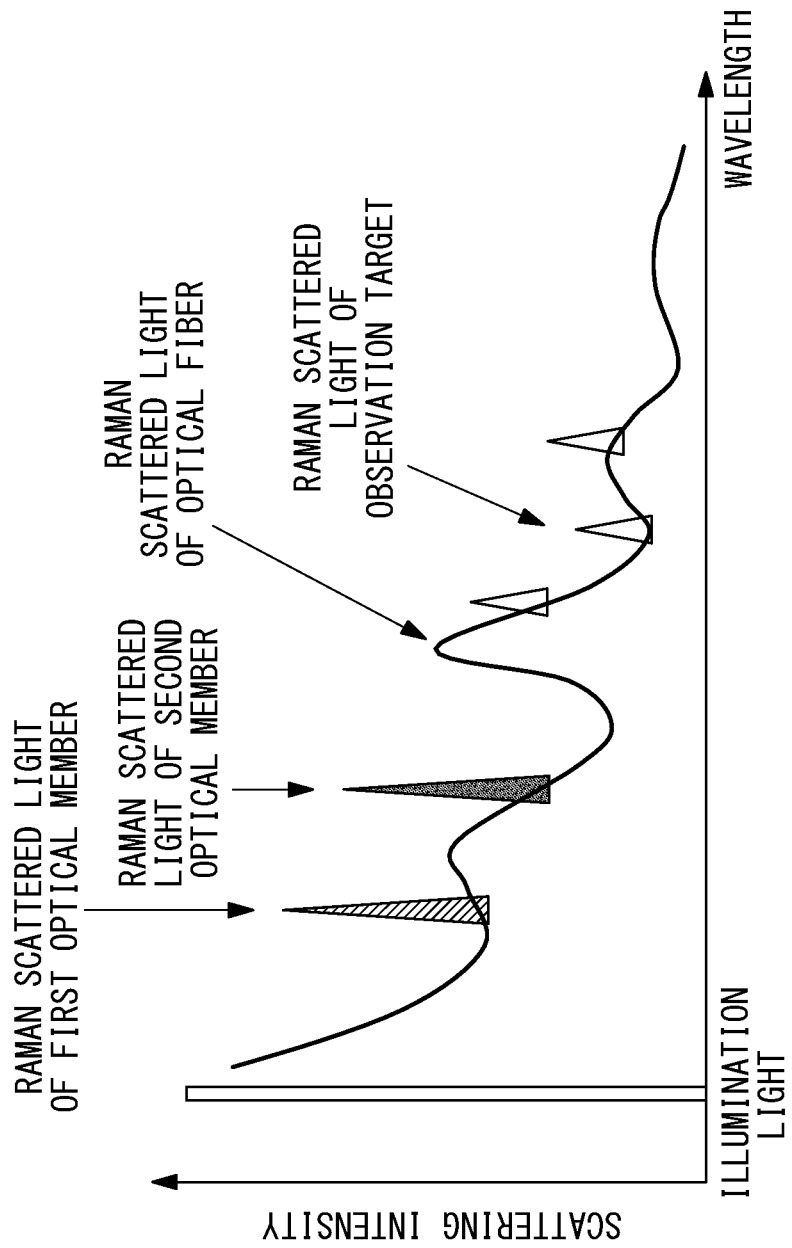
FIG. 34 is a diagram for explaining a spectrum of return light traveling from an optical probe side to a spectroscopic analysis portion side in the diagnosis mode of the observation target, the diagnosis mode being performed by employing the spectroscopic analysis apparatus in FIG. 32.

FIG. 34 is a diagram that schematically shows the spectrum of the light that returns toward the spectroscopic analysis portion 3 from an optical probe 51 side, and a Raman scattered light beam that is generated while the illumination light is being guided through the optical fiber 4 of the optical probe 51, a Raman scattered light beam that is generated when the illumination light passes through the first optical member 7 and the second optical member 22c, a Raman scattered light beam (signal light) that is generated at the observation target X, and a portion of the illumination light return toward the spectroscopic analysis portion 3 from the optical probe 51 side as return light.

Figure 35:
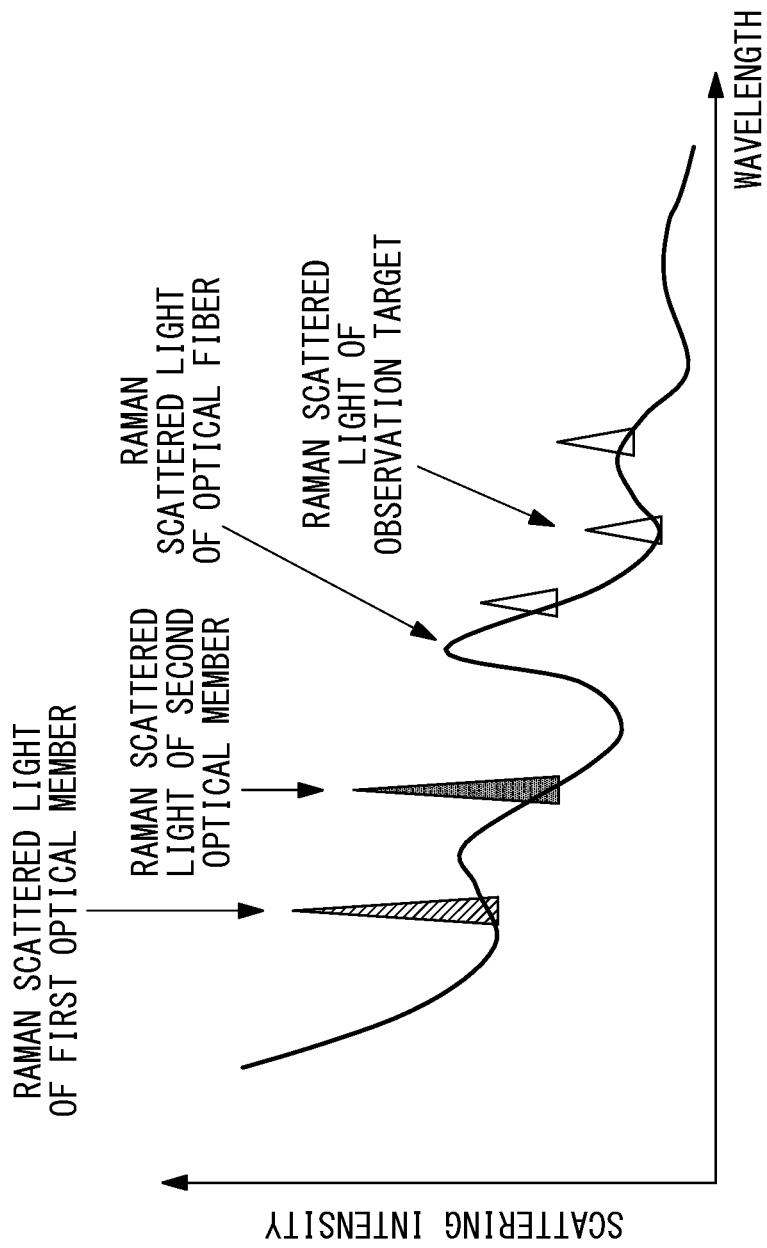
FIG. 35 is a diagram for explaining a measurement of a spectrum of light entering a spectroscopic measurement portion in the diagnosis mode of the observation target, the diagnosis mode being performed by employing the spectroscopic analysis apparatus in FIG. 32.

Because the dichroic mirror 11 allows the illumination light to pass therethrough, as in the optical spectrum shown in FIG. 35, the illumination light beam among the return light is removed by passing through the dichroic mirror 11, the examination light consisting of the Raman scattered light beams of the observation target X, the first optical member 7, the second optical member 22c, and the optical fiber 4 is reflected and enters the spectroscopic measurement portion 12.

In the diagnosis mode, the computation portion 14 removes, in the same method as in the above-described embodiments, the contributions of the Raman scattered light beams generated at the first optical member 7, the second optical member 22c, and the optical fiber 4 from the input Raman spectrum of the return light, and thus, the computation portion 14 acquires the Raman spectrum of the observation target X.

Figure 36:
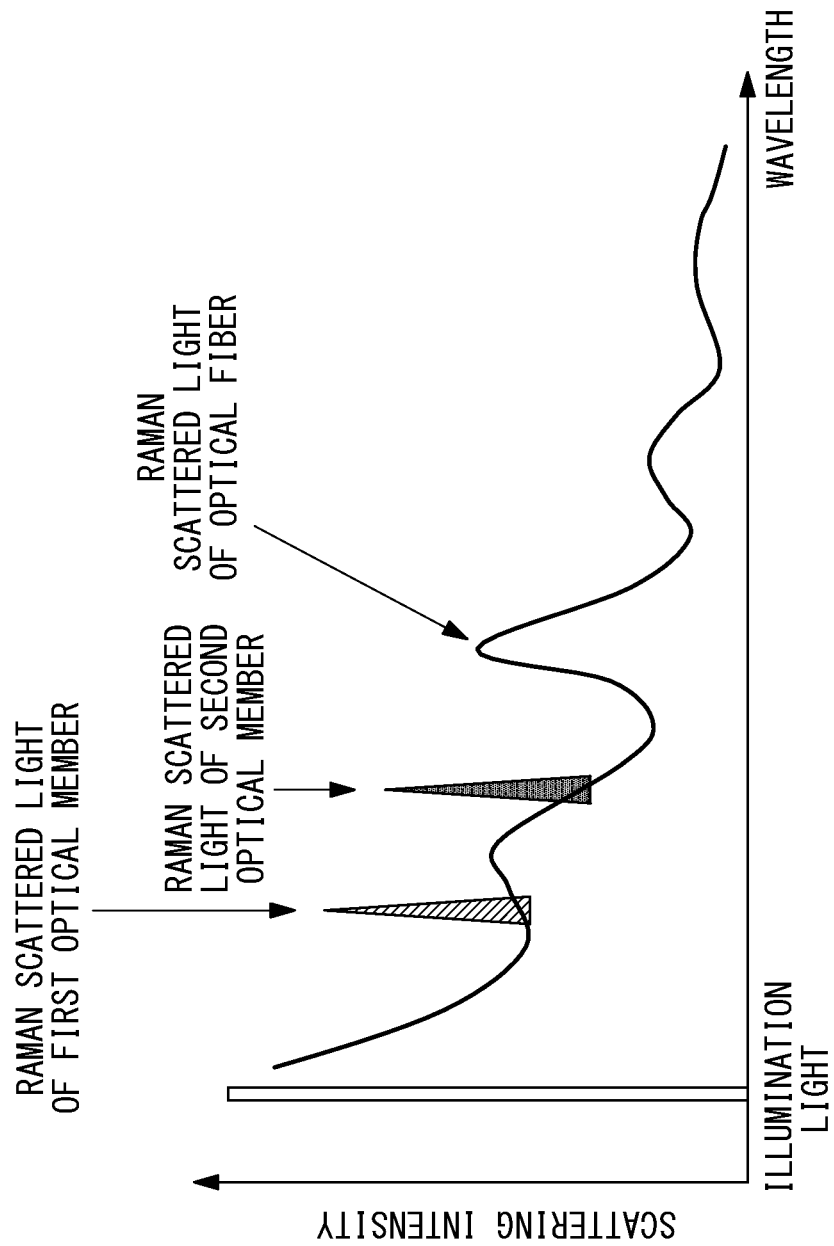
FIG. 36 is a diagram for explaining a measurement of a spectrum of light entering the spectroscopic measurement portion in the examination mode of the observation target, the examination mode being performed by employing the spectroscopic analysis apparatus in FIG. 32.

In the examination mode, the illumination light is emitted from the light source 10 without disposing the observation target X at the distal end of the optical probe 51. FIG. 36 is a diagram that schematically shows the spectrum of the light returning toward the spectroscopic analysis portion 3 from the optical probe 51 side in the examination mode, and the illumination light beam reflected by the first optical member 7, the Raman scattered light beam generated when the illumination light is guided through the first optical member 7 and the second optical member 22c, and the Raman scattered light beam generated at the optical fiber 4 return toward the spectroscopic analysis portion 3 from the optical probe 51 side as the return light.

Also, because the dichroic mirror 11 allows the illumination light to pass therethrough, the illumination light in the return light is removed as a result of passing therethrough, the examination light consisting of the Raman scattered light beams of the first optical member 7, the second optical member 22c, and the optical fiber 4 is reflected and is made to enter to the spectroscopic measurement portion 12.

Figure 37:
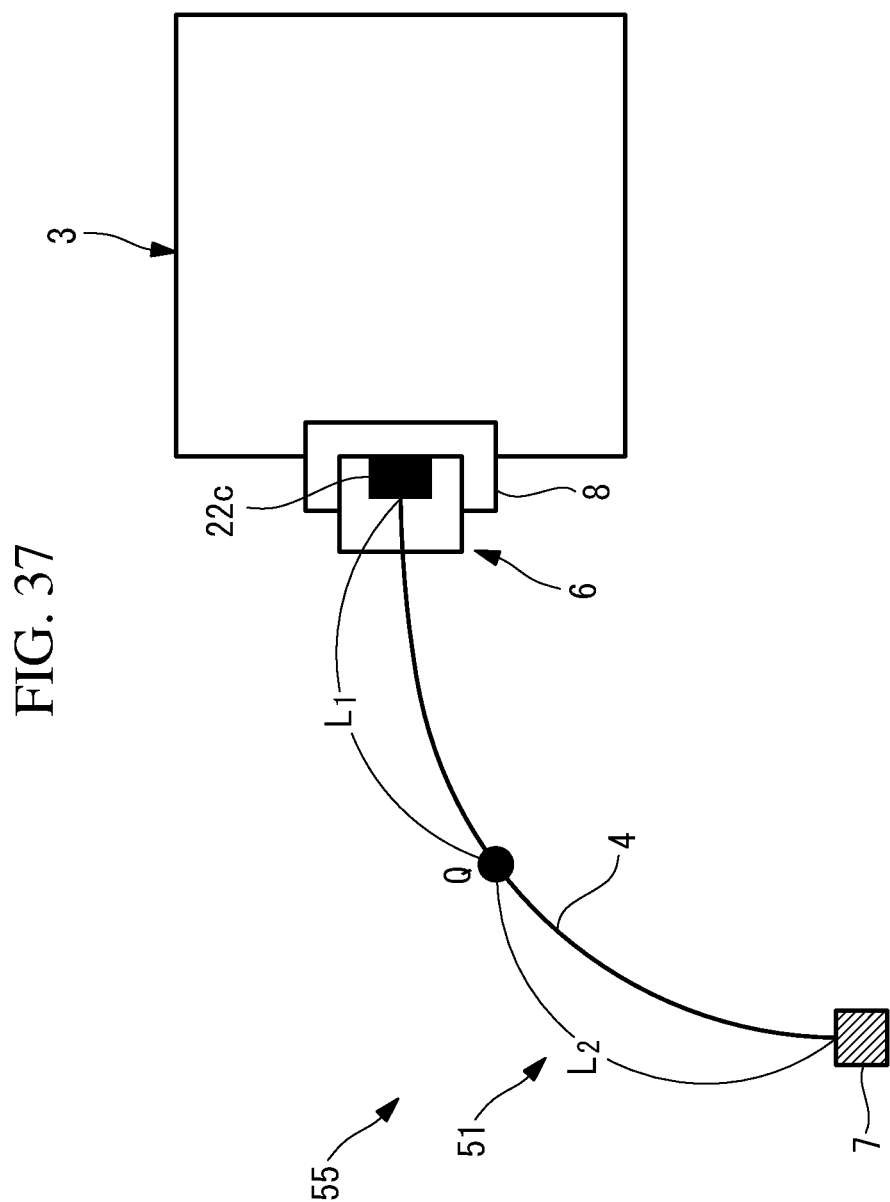
FIG. 37 is a schematic diagram showing the relationship between the arrangement of a first optical member, a second optical member, the optical fiber, a connector, and a receiving-side connector and the position of a point Q at which the optical transmission efficiency changes in the optical fiber in the examination mode of the observation target, the examination mode being performed by employing the spectroscopic analysis apparatus in FIG. 32.

Here, the Raman spectral intensities of the examination light detected by the spectroscopic measurement portion 12 will be described. FIG. 37 schematically shows the arrangement of the spectroscopic analysis portion 3, the connector 6 of the optical probe 51, the receiving-side connector 8 of the spectroscopic analysis portion 3, the optical fiber 4 built into the optical probe 51, the first optical member 7, and the second optical member 22c in this embodiment. A change in the optical transmission efficiency is assumed to be occurring, due to damage to the optical fiber 4, at the position of the point Q on the optical probe 51.

The length of the optical fiber 4 from the connecting position of the optical probe 51 and the spectroscopic analysis portion 3 to the position of the point Q is assumed to be $L_1$, and the length of the optical fiber 4 from the position of the point Q to the first optical member 7 disposed at the distal end of the optical probe 51 is assumed to be $L_2$. The total length of the optical fiber 4 is assumed to be L ($L=L_1+L_2$).

Here, the optical transmission efficiency of the optical connection of the spectroscopic analysis portion 3 and the optical probe 51 is assumed to be $\eta(0<\eta<1)$, the optical transmission efficiency at the position of the point Q is assumed to be $\alpha(0<\alpha<1)$, and the light reflection efficiency at a distal-end surface of the optical probe 51 is assumed to be $\gamma(0<\gamma<1)$.

The Raman-scattered-light generation efficiency in the first optical member 7 is assumed to be $\sigma_1$, the Raman-scattered-light generation efficiency in the second optical member 22c is assumed to be $\sigma_2$, and the Raman-scattered-light generation efficiency in the optical fiber 4 of the optical probe 51 is assumed to be $\sigma_g$. The optical input power to the optical probe 51 from the spectroscopic analysis portion 3 is assumed to be P.

When the various parameters are determined as described above, of the examination light detected by the spectroscopic measurement portion 12, the light intensity due to the Raman scattering of various members is approximated by a sum of intensities of light components of Expression (13) to Expression (15) below.

Of the Raman scattered light generated by the illumination light guided to the distal end of the optical probe 51 from the proximal end thereof, a light component $L_{T1}$ that returns to the spectroscopic analysis portion 3 without passing through the distal end of the optical probe 51 is expressed by Expression (13) below.

$$L_{T1}=\sigma_2\eta^2P+L_1\sigma_g\eta^2P+L_2\sigma_g\alpha^2\eta^2P+\sigma_1\alpha^2\eta^2P \quad (13)$$

Of the Raman scattered light generated by the illumination light guided to the distal end of the optical probe 51 from the proximal end thereof, a light component $L_{T2}$ that returns to the spectroscopic analysis portion 3 by being reflected at the distal end of the optical probe 51 is expressed by Expression (14) below.

$$L_{T2}=\gamma\alpha^2\eta^2P(\sigma_1+\sigma_2+\sigma_g L) \quad (14)$$

Of the Raman scattered light generated by the illumination light guided to the proximal end of the optical probe 51 from the distal end thereof, a light component $L_{T3}$ that returns to the spectroscopic analysis portion 3 without passing through the distal end of the optical probe 51 is expressed by Expression (15) below.

$$L_{T3}=\gamma\alpha^2\eta^2P(\sigma_1+\sigma_2+\sigma_g L) \quad (15)$$

Therefore, the Raman scattering intensity Pobs detected by the spectroscopic measurement portion 12 is approximated by Expression (16) below.

$$\begin{aligned}Pobs = {} & \sigma_2\eta^2P + L_1\sigma_g\eta^2P + \\ & L_2\sigma_g\alpha^2\eta^2P + \sigma_1\alpha^2\eta^2P + 2\gamma\alpha^2\eta^2P(\sigma_1+\sigma_2+\sigma_g L) = \\ & (1+2\gamma)\alpha^2\eta^2P\sigma_1 + (1+2\gamma\alpha^2)\eta^2P\sigma_2 + (L_1\eta^2 + L_2\alpha^2\eta^2 + 2\gamma\alpha^2\eta^2L)P\sigma_g\end{aligned} \quad (16)$$

Here, because the Raman scattering intensity detected by the spectroscopic measurement portion 12 varies depending on the optical connection realized between the receiving-side connector 8 of the spectroscopic analysis portion 3 and the connector 6 of the optical probe 51 or the optical-fiber optical power loss in the optical probe 51, it is possible to identify a specific site at which a optical power loss problem is occurring on the basis of the Raman spectrum of the examination light. This fact will be explained below, in detail, by way of cases 1 to 4 with different conditions.

Case 1

The case in which optical power losses in the spectroscopic analysis portion 3 and the connector 6 of the optical probe 51 are negligible and an power loss at optical fiber in the optical probe 51 is also negligible, in other words, the case in which $\eta\approx 1$ and $\alpha\approx 1$, will be described.

In this case, the total Raman scattering intensity ST1 detected by the spectroscopic measurement portion 12 is expressed by Expression (17) below.

$$ST1 = (1+2\gamma)P\sigma_1 + (1+2\gamma)P\sigma_2 + (L_1+L_2+2\gamma L)P\sigma_g \quad (17)$$

R112, which is the ratio of the Raman scattering intensity of the first optical member 7 and the Raman scattering intensity of the second optical member 22c, is expressed by Expression (18) below.

$$R112 = (1 + 2\gamma)P\sigma_1/(1 + 2\gamma)P\sigma_2 = \sigma_1/\sigma_2 \quad (18)$$

Case 2

The case in which optical power lossese in the spectroscopic analysis portion 3 and the connector 6 of the optical probe 51 are present and the power loss at optical fiber in the optical probe 51 is negligible, in other words, the case in which $0<\eta<1$ and $\alpha \approx 1$, will be described.

In this case, the total Raman scattering intensity ST2 detected by the spectroscopic measurement portion 12 is expressed by Expression (19) below.

$$ST2 = 2\gamma\eta^2 P\sigma_1 + (\eta^2 + \eta^2 + 2\gamma\eta^2)P\sigma_2 + (L_1\eta^2 + L_2\eta^2 + 2\gamma\eta^2 L)P\sigma_g = \quad (19)$$
$$((1 + 2\gamma)P\sigma_1 + (1 + 2\gamma)P\sigma_2 + (L_1 + L_2 + 2\gamma L)P\sigma_g)\eta^2 = \eta^2 ST1$$

R212, which is the ratio of the Raman scattering intensity of the first optical member 7 and the Raman scattering intensity of the second optical member 22c, is expressed by Expression (20) below.

$$R212 = (1 + 2\gamma)P\sigma_1/(1 + 2\gamma)\sigma_2 P = \sigma_1/\sigma_2 \quad (20)$$

Case 3

The case in which optical power losses in the spectroscopic analysis portion 3 and the connector 6 of the optical probe 51 are negligible and an power loss at optical fiber in the optical probe 51 is present, in other words, the case in which $\eta \approx 1$ and $0<\alpha<1$, will be described.

In this case, the total Raman scattering intensity ST3 detected by the spectroscopic measurement portion 12 is expressed by Expression (21) below.

$$ST3 = (1 + 2\gamma)\alpha^2 P\sigma_1 + (1 + 2\gamma\alpha^2)P\sigma_2 + (L_1 + L_2\alpha^2 + 2\gamma\alpha^2 L)P\sigma_g \quad (21)$$

In Case 3, R312, which is the ratio of the Raman scattering intensity of the first optical member 7 and the Raman scattering intensity of the second optical member 22c, is expressed by Expression (22) below.

$$R312 = (1+2\gamma)\alpha^2\sigma_1/(1+2\gamma\alpha^2)\sigma_2 \quad (22)$$

Case 4

The case in which optical power losses in the spectroscopic analysis portion 3 and the connector 6 of the optical probe 51 are present and optical power loss in the optical fiber 4 is also present, in other words, the case in which $0<\eta<1$ and $0<\alpha<1$, will be described.

In this case, the total Raman scattering intensity ST4 detected by the spectroscopic measurement portion 12 is expressed by Expression (23) below.

$$ST4 = 2\gamma\alpha^2\eta^2 P\sigma_1 + \quad (23)$$
$$(1 + \alpha^2 + 2\gamma\alpha^2)\eta^2 P\sigma_2 + (L_1 + L_2\alpha^2 + 2\gamma\alpha^2 L)\eta^2 P\sigma_g = \eta^2 ST3$$

R412, which is the ratio of the Raman scattering intensity of the first optical member 7 and the Raman scattering intensity of the second optical member 22c, is expressed by Expression (24) below.

$$R412=(1+2\gamma)\alpha^2\sigma_1/(1+2\gamma\alpha^2)\sigma_2 \quad (24)$$

In Case 2, the Raman scattering intensity ST2 detected by the spectroscopic measurement portion 12 decreases, with respect to the Raman scattering intensity ST1 detected by the spectroscopic measurement portion 12 in Case 1, by a factor contribution corresponding to the square of the transmission efficiency $\eta(0<\eta<1)$. On the other hand, the Raman scattering intensity ratio R112 of the first optical member 7 and the second optical member 22c in Case 1 and the Raman scattering intensity ratio R212 of the first optical member 7 and the second optical member 22c in Case 2 are the same values.

Here, as an intermediate value between ST1 and ST2, it is possible to set an appropriate threshold TS1. As in this Case 2, when the total Raman scattering intensity is less than the threshold TS1 and the Raman scattering intensity ratio of the first optical member 7 and the second optical member 22c is no different as compared with Case 1, the computation portion 14 determines that, although the problem of large optical power loss is occurring at the connection between the receiving-side connector 8 and the connector 6, the optical fiber 4 is normal.

In Case 3, the total Raman scattering intensity ST3 detected by the spectroscopic measurement portion 12 decreases with respect to the total Raman scattering intensity ST1 detected by the spectroscopic measurement portion 12 in Case 1, and, furthermore, the Raman scattering intensity ratio R312 of the first optical member 7 and the second optical member 22c also decreases as compared with R112 (and R212).

In Case 4, the total Raman scattering intensity ST4 detected by the spectroscopic measurement portion 12 additionally decreases by a factor contribution corresponding to the square of the transmission efficiency $\eta(0<\eta<1)$ with respect to the Raman scattering intensity ST3 detected by the spectroscopic measurement portion 12 in Case 3. On the other hand, the Raman scattering intensity ratio R412 of the first optical member 7 and the second optical member 22c is the same value as R312.

In Case 3 and Case 4, the total Raman scattering intensity decreases and the Raman scattering intensity ratio of the first optical member 7 and the second optical member 22c also decreases. Therefore, when the optical power loss in the optical fiber 4 and the optical power loss in the connector 6 are in the prescribed conditions, R112 and R312 are measured in advance, and an appropriate threshold TR is set between values of R112 and R312. Accordingly, it is possible to distinguish Case 3 and Case 4 from states of Case 1 (optical power losses are negligible at the connector 6 and the optical fiber 4) and Case 2 (optical power loss is occurring at the connector 6 and the optical power loss at the optical fiber 4 is normal) on the basis of the Raman scattering intensity ratio of the first optical member 7 and the second optical member 22c.

In Case 4, because the total Raman scattering intensity further decreases as compared with Case 3, it is possible to distinguish a state in Case 4 and a state in Case 3 on the basis of the total Raman scattering intensity by setting an appropriate threshold TS2 between the values of ST3 and ST4.

As a result of setting the thresholds in this way, in the case in which the total Raman scattering intensity is greater than the threshold TS2 and the Raman scattering intensity ratio is less than the threshold TR, the computation portion 14 determines that, although the connection between the receiving-side connector 8 and the connector 6 is normal, the problem of large optical power loss is occurring at the optical fiber 4.

In the case in which the Raman scattering intensity is less than the threshold TS2 and the Raman scattering intensity ratio is less than the threshold TR, the computation portion 14 determines that the problem of large optical power loss is occurring at the connection between the receiving-side connector 8 and the connector 6 and the problem of large optical power loss is occurring at the optical fiber 4.

With the first embodiment of the present invention, the sum and the ratio of the Raman scattering intensity of the first optical member 7 and the Raman scattering intensity of the optical fiber 4 of the optical probe 2 are used in the optical power loss examination. In the first embodiment, in the case in which optical power loss, due to fiber damage, is occurring in the vicinity of the proximal end of the optical probe 2 in the optical fiber 4 in the optical probe 2, when there are (A) a situation in which, although the connector connection between the optical probe 2 and the spectroscopic analysis portion 3 is normal, abnormal optical power loss is occurring at the optical probe 2 and (B) a situation in which, although abnormal optical power loss is occurring at the connector connection between the optical probe 2 and the spectroscopic analysis portion 3, the optical power loss at the optical probe 2 is normal, it may not be easy to make distinction between these problems, because the ratio of the Raman scattering intensity of the first optical member 7 and the Raman scattering intensity of the optical fiber 4 of the optical probe 2 in the situation (A) differs only slightly from that in the situation (B).

However, with this embodiment, as a result of separately calculating the sum of the Raman scattering intensities due to the materials and the ratio of the Raman scattering intensities of the first optical member 7 and the second optical member 22*c* from the Raman scattered light beams generated at the first optical member 7 disposed at the distal end of the optical probe 51, the second optical member 22*c* disposed at the proximal end of the optical probe 51, and the optical fiber 4, there is an advantage in that it is possible to accurately determine whether a problem due to the optical power loss is occurring in the optical fiber 4 in the optical probe 51 due to a failure in the connector 6 that connects the spectroscopic analysis portion 3 to the optical probe 51 or in the optical fiber 4 built into the optical probe 51, regardless of the region in which the optical power loss due to fiber damage is occurring.

As a result, the following aspect is read from the above described embodiment of the present invention.

An aspect of the present invention is a spectroscopic analysis apparatus including: an optical probe; and a spectroscopic analysis portion to which the optical probe is attached in an attachable/detachable manner by means of a connector, wherein the optical probe includes an optical fiber that guides illumination light coming from a light source and signal light coming from an observation target and an optical member that is disposed at least at a distal end of the optical fiber, and the spectroscopic analysis portion includes an information separation portion that generates wavelength dependent characteristics by optically dispersing the signal light and that separates, from information about the signal light, information about first return light returning from the optical member and second return light returning from the optical fiber, a problem determining portion that determines a problem occurring at the optical probe on the basis of the first return light and the second return light separated by the information separation portion, and a notification portion that notifies information about the determined problem.

With this aspect, when the optical probe is connected to the spectroscopic analysis portion by means of the connector, the illumination light coming from the light source is radiated onto the observation target by passing through the optical member at the distal end of the optical probe via the optical fiber. The signal light generated at the observation target passes through the optical member, is guided by the optical fiber, and is input to the spectroscopic analysis portion. Meanwhile, the first return light returns from the optical member disposed at the distal end of the optical fiber due to the irradiation with the illumination light, and the second return light returns from the optical fiber. In the spectroscopic analysis portion, the first return light beam and the second return light beam are separated from the input light, and the remaining signal light is optically dispersed to generate the wavelength dependent characteristics.

Meanwhile, the information about the first return light and the information about the second return light, separated from the signal light, are separated by the information separation portion and are used in the problem determination by the problem determining portion. Then, a notification about the information about the problem determined by the problem determining portion is notified by the notification portion. Accordingly, even if a medical personnel who operates the spectroscopic analysis apparatus does not have detailed knowledge, he/she can deal with a problem by identifying a site of the problem.

Another aspect of the present invention is a spectroscopic analysis apparatus including: an optical probe; and a spectroscopic analysis portion to which the optical probe is attached in an attachable/detachable manner by means of a connector, wherein the optical probe includes an optical fiber that guides illumination light coming from a light source and signal light coming from an observation target and optical members that are disposed at a distal end and a proximal end of the optical fiber, and the spectroscopic analysis portion includes an information separation portion that generates wavelength dependent characteristics by optically dispersing the signal light and that separates, from information about the signal light, information about first return light returning from the optical member at the distal end and second return light returning from the optical member at the proximal end, a problem determining portion that determines a problem occurring at the optical probe on the basis of the first return light and the second return light separated by the information separation portion, and a notification portion that notifies information about the determined problem.

With this aspect, when the optical probe is connected to the spectroscopic analysis portion by means of the connector, the illumination light coming from the light source is radiated onto the observation target by passing through the optical member at the distal end of the optical probe via the optical fiber. The signal light generated at the observation target passes through the optical member, is guided by the optical fiber, and is input to the spectroscopic analysis portion. Meanwhile, the first return light returns from the optical member disposed at the distal end of the optical fiber due to the irradiation with the illumination light, and the second return light returns from the optical member disposed at the proximal end of the optical fiber. In the spectroscopic analysis portion, the first return light beam and the second return light beam are separated from the input light, and the remailing signal light is optically dispersed to generate the wavelength dependent characteristics.

Meanwhile, the information about the first return light and the information about the second return light, separated from the signal light, are separated by the information separation portion and are used in the problem determination by the problem determining portion. Then, a notification about the information about the problem determined by the problem determining portion is notified by the notification portion. Accordingly, even if a medical personnel who operates the spectroscopic analysis apparatus does not have detailed knowledge, he/she can deal with a problem by identifying a site of the problem.

In the above-described aspect, the first return light beam and the second return light beam may be fluorescence beams.

In the above-described aspect, the first return light beam and the second return light beam may be Raman scattered light beams.

In the above-described aspect, the problem determining portion may determine a problem on the basis of a sum of the intensity of the first return light and the intensity of the second return light and a ratio of the intensity of the first return light and the intensity of the second return light.

With this configuration, in the case in which there is no problem, the sum of the intensity of the first return light and the intensity of the second return light is greater than a prescribed threshold, and, in the case in which there is a problem, the sum of the intensity of the first return light and the intensity of the second return light is equal to or less than the prescribed threshold.

On the other hand, in the case in which the optical member is present at the proximal end of the optical fiber, the ratio of the intensity of the first return light with respect to the intensity of the second return light is greater than a prescribed threshold in the case in which there is no problem. The ratio of the intensity of the first return light with respect to the intensity of the second return light is less than the prescribed threshold in the case in which a problem is occurring in a portion from the connector to the distal end of the optical fiber.

In the case in which the optical member is not present at the proximal end of the optical fiber, the ratio of the intensity of the first return light with respect to the intensity of the second return light is less than the prescribed threshold in the case in which there is no problem. The ratio of the intensity of the first return light with respect to the intensity of the second return light is greater than the prescribed threshold in the case in which a problem is occurring in a portion from the connector to the distal end of the optical fiber.

Accordingly, it is possible to determine problems by distinguishing the case in which there is no problem, the case in which a problem is occurring at the connector, and the case in which a problem is occurring in a portion from the connector to the distal end of the optical fiber, and thus, it is possible to notify more detailed information by means of the notification portion.

In the above-described aspect, problems occurring in a plurality of the optical fibers of the optical probe may be determined by utilizing two or more wavelengths of a spectrum of the first return light returning from the optical member at the distal end of the optical fibers.

REFERENCE SIGNS LIST 1, 20, 32, 44 spectroscopic analysis apparatus
2, 21, 33, 51 optical probe
3, 24, 38, 45 spectroscopic analysis portion
4 optical fiber
6, 36, 37 connector
7 first optical member (optical member)
10 light source
14 computation portion (information separation portion, problem determining portion)
15 display portion (notification portion)
22a second optical member (optical member)
22b third optical member (optical member)
25 diagnosis light source (light source)
26 examination light source (light source)
34 illumination fiber (optical fiber)
35 light collecting fiber (optical fiber)
X observation target

The invention claimed is:
1. A spectroscopic analysis apparatus comprising:
an optical probe; and
a spectroscopic analysis portion to which the optical probe is attached in an attachable/detachable manner by means of a connector,
wherein the optical probe comprises:
an optical fiber configured to guide illumination light coming from a light source and signal light coming from an observation target; and
an optical member disposed at least at a distal end of the optical fiber, and
wherein the spectroscopic analysis portion comprises a processor comprising hardware, the processor being configured to:
generate wavelength dependent characteristics by optically dispersing the signal light and to separate, from information about the signal light, information about first return light returning from the optical member and second return light returning from the optical fiber;
determine a problem occurring at the optical probe on the basis of the separated first return light and the second return light; and
control a display to notify information about the determined problem;
wherein the processor determines the problem on the basis of a sum of the intensity of the first return light and the intensity of the second return light and a ratio of the intensity of the first return light and the intensity of the second return light.
2. A spectroscopic analysis apparatus according to claim 1, wherein problems occurring in a plurality of the optical fibers of the optical probe are determined by utilizing two or more wavelengths of a spectrum of the first return light returning from the optical member at the distal end of the optical fibers.
3. A spectroscopic analysis apparatus comprising:
an optical probe; and
a spectroscopic analysis portion to which the optical probe is attached in an attachable/detachable manner by means of a connector,
wherein the optical probe comprises:
an optical fiber configured to guide illumination light coming from a light source and signal light coming from an observation target; and
optical members disposed at a distal end and a proximal end of the optical fiber, and
wherein the spectroscopic analysis portion comprises a processor comprising hardware, the processor being configured to:

generate wavelength dependent characteristics by optically dispersing the signal light and to separate, from information about the signal light, information about first return light returning from the optical member at the distal end and second return light returning from the optical member at the proximal end;

determine a problem occurring at the optical probe on the basis of the separated first return light and the second return light; and control a display to notify information about the determined problem;

wherein the processor determines the problem on the basis of a sum of the intensity of the first return light and the intensity of the second return light and a ratio of the intensity of the first return light and the intensity of the second return light.

4. A spectroscopic analysis apparatus comprising:

an optical probe; and a spectroscopic analysis portion to which the optical probe is attached in an attachable/detachable manner by means of a connector, wherein the optical probe comprises:

an optical fiber configured to guide illumination light coming from a light source and signal light coming from an observation target; and optical members disposed at a distal end and a proximal end of the optical fiber, and wherein the spectroscopic analysis portion comprises a processor comprising hardware, the processor being configured to:

generate wavelength dependent characteristics by optically dispersing the signal light and to separate, from information about the signal light, information about first return light returning from the optical member at the distal end and second return light returning from the optical member at the proximal end;

determine a problem occurring at the optical probe on the basis of the separated first return light and the second return light; and control a display to notify information about the determined problem;

wherein problems occurring in a plurality of the optical fibers of the optical probe are determined by utilizing two or more wavelengths of a spectrum of the first return light returning from the optical member at the distal end of the optical fibers.

* * * * *